United States Patent
Markovic et al.

(10) Patent No.: US 11,305,020 B2
(45) Date of Patent: *Apr. 19, 2022

(54) METHODS FOR REDUCING TOXICITY OF A CHEMOTHERAPEUTIC DRUG

(71) Applicant: Mayo Foundation for Medical Education and Research, Rochester, MN (US)

(72) Inventors: Svetomir N. Markovic, Rochester, MN (US); Wendy K. Nevala, Rochester, MN (US)

(73) Assignee: MAYO FOUNDATION FOR MEDICAL EDUCATION AND RESEARCH, Rochester, MN (US)

( * ) Notice: Subject to any disclaimer, the term of this patent is extended or adjusted under 35 U.S.C. 154(b) by 628 days.

This patent is subject to a terminal disclaimer.

(21) Appl. No.: 16/086,978

(22) PCT Filed: Mar. 21, 2017

(86) PCT No.: PCT/US2017/023443
§ 371 (c)(1),
(2) Date: Sep. 20, 2018

(87) PCT Pub. No.: WO2017/165440
PCT Pub. Date: Sep. 28, 2017

(65) Prior Publication Data
US 2019/0099498 A1    Apr. 4, 2019

Related U.S. Application Data

(60) Provisional application No. 62/311,327, filed on Mar. 21, 2016.

(51) Int. Cl.
| | |
|---|---|
| *A61K 39/395* | (2006.01) |
| *A61K 47/64* | (2017.01) |
| *C07K 16/28* | (2006.01) |
| *A61K 31/337* | (2006.01) |
| *A61K 47/68* | (2017.01) |
| *A61K 47/69* | (2017.01) |
| *C07K 16/30* | (2006.01) |
| *A61P 35/00* | (2006.01) |
| *A61K 45/06* | (2006.01) |
| *C07K 16/22* | (2006.01) |
| *C07K 16/24* | (2006.01) |
| *C07K 16/42* | (2006.01) |
| *A61K 9/00* | (2006.01) |

(52) U.S. Cl.
CPC .......... *A61K 47/643* (2017.08); *A61K 31/337* (2013.01); *A61K 39/3955* (2013.01); *A61K 45/06* (2013.01); *A61K 47/6867* (2017.08); *A61K 47/6929* (2017.08); *A61P 35/00* (2018.01); *C07K 16/22* (2013.01); *C07K 16/244* (2013.01); *C07K 16/249* (2013.01); *C07K 16/2806* (2013.01); *C07K 16/2809* (2013.01); *C07K 16/2827* (2013.01); *C07K 16/2842* (2013.01); *C07K 16/2845* (2013.01); *C07K 16/2878* (2013.01); *C07K 16/2887* (2013.01); *C07K 16/2893* (2013.01); *C07K 16/3061* (2013.01); *C07K 16/4208* (2013.01); *C07K 16/4291* (2013.01); *A61K 9/0019* (2013.01); *C07K 2317/24* (2013.01)

(58) Field of Classification Search
None
See application file for complete search history.

(56) References Cited

U.S. PATENT DOCUMENTS

| | | |
|---|---|---|
| 4,350,687 A | 9/1982 | Lipton et al. |
| 5,026,772 A | 6/1991 | Kobayashi et al. |
| 5,116,944 A | 5/1992 | Sivam et al. |
| 5,216,130 A | 6/1993 | Line et al. |
| 5,252,713 A | 10/1993 | Morgan, Jr. et al. |
| 5,260,308 A | 11/1993 | Poduslo et al. |
| 5,728,541 A | 3/1998 | Kornblith |
| 5,736,137 A | 4/1998 | Anderson et al. |
| 6,054,297 A | 4/2000 | Carter et al. |
| 6,147,060 A | 11/2000 | Zasloff et al. |
| 6,416,967 B2 | 7/2002 | Kornblith |
| 6,537,579 B1 | 3/2003 | Desai et al. |
| 6,933,129 B1 | 8/2005 | Kornblith |
| 7,041,301 B1 | 5/2006 | Markovic |
| 7,112,409 B2 | 9/2006 | Blumenthal et al. |
| 7,678,552 B2 | 3/2010 | Kornblith |
| 7,731,950 B2 | 6/2010 | Noessner et al. |
| 7,758,891 B2 | 7/2010 | Desai et al. |
| 7,820,788 B2 | 10/2010 | Desai et al. |
| 7,906,121 B2 | 3/2011 | Chang et al. |
| 7,923,536 B2 | 4/2011 | Desai et al. |

(Continued)

FOREIGN PATENT DOCUMENTS

| | | |
|---|---|---|
| EP | 1913947 | 4/2008 |
| EP | 3204413 | 8/2017 |

(Continued)

OTHER PUBLICATIONS

U.S. Appl. No. 15/187,672, office action dated Sep. 11, 2019.

(Continued)

*Primary Examiner* — Yunsoo Kim
(74) *Attorney, Agent, or Firm* — Baker Botts L.L.P.

(57) ABSTRACT

This disclosure relates to methods for improving the therapeutic index of a chemotherapeutic drug in the treatment of patients afflicted with cancer, by reducing chemotherapy-related toxicity to a level that allows the chemotherapeutic drug to be used in humans.

16 Claims, 1 Drawing Sheet

(56) References Cited

U.S. PATENT DOCUMENTS

| | | |
|---|---|---|
| 8,034,375 B2 | 10/2011 | Desai et al. |
| 8,119,129 B2 | 2/2012 | Jure-Kunkel et al. |
| 8,138,229 B2 | 3/2012 | Desai et al. |
| 8,268,348 B2 | 9/2012 | Desai et al. |
| 8,314,156 B2 | 11/2012 | Desai et al. |
| 8,344,177 B2 | 1/2013 | Neri et al. |
| 8,735,394 B2 | 5/2014 | Desai et al. |
| 8,853,260 B2 | 10/2014 | Desai et al. |
| 9,101,543 B2 | 8/2015 | Desai et al. |
| 9,387,244 B2 | 7/2016 | Markovic |
| 9,427,477 B2 | 8/2016 | Markovic et al. |
| 9,446,148 B2 | 9/2016 | Markovic et al. |
| 9,533,058 B2 | 1/2017 | Markovic et al. |
| 9,555,128 B2 | 1/2017 | Markovic et al. |
| 9,566,350 B2 | 2/2017 | Markovic et al. |
| 9,757,453 B2 | 9/2017 | Markovic et al. |
| 10,279,035 B2 | 5/2019 | Markovic et al. |
| 10,279,036 B2 | 5/2019 | Markovic et al. |
| 10,300,016 B2 | 5/2019 | Markovic et al. |
| 10,307,482 B2 | 6/2019 | Markovic et al. |
| 10,322,084 B2 | 6/2019 | Markovic et al. |
| 10,376,579 B2 | 8/2019 | Markovic et al. |
| 10,376,580 B2 | 8/2019 | Markovic et al. |
| 10,391,055 B2 | 8/2019 | Markovic et al. |
| 10,406,224 B2 | 9/2019 | Markovic et al. |
| 10,413,606 B2 | 9/2019 | Markovic et al. |
| 10,420,839 B2 | 9/2019 | Markovic et al. |
| 10,441,656 B2 | 10/2019 | Markovic et al. |
| 10,471,145 B2 | 11/2019 | Markovic et al. |
| 10,478,495 B2 | 11/2019 | Markovic et al. |
| 10,493,150 B2 | 12/2019 | Markovic et al. |
| 10,507,243 B2 | 12/2019 | Markovic et al. |
| 10,561,726 B2 | 2/2020 | Swiss et al. |
| 10,596,111 B2 | 3/2020 | Markovic et al. |
| 10,596,112 B2 | 3/2020 | Markovic et al. |
| 10,610,484 B2 | 4/2020 | Markovic et al. |
| 10,618,969 B2 | 4/2020 | Markovic et al. |
| 10,624,846 B2 | 4/2020 | Markovic et al. |
| 10,668,151 B2 | 6/2020 | Markovic et al. |
| 10,765,741 B2 | 9/2020 | Markovic et al. |
| 10,772,633 B2 | 9/2020 | Markovic et al. |
| 10,780,049 B2 | 9/2020 | Markovic et al. |
| 10,780,050 B2 | 9/2020 | Markovic et al. |
| 2002/0111362 A1 | 8/2002 | Rubinfeld |
| 2004/0005318 A1 | 1/2004 | Davis et al. |
| 2004/0077601 A1 | 4/2004 | Adams et al. |
| 2005/0032699 A1 | 2/2005 | Holash et al. |
| 2006/0165652 A1 | 7/2006 | Dudley et al. |
| 2007/0020232 A1 | 1/2007 | Rossignol et al. |
| 2007/0148135 A1 | 6/2007 | Dang et al. |
| 2007/0166388 A1 | 7/2007 | Desai et al. |
| 2009/0004118 A1 | 1/2009 | Nie et al. |
| 2010/0047234 A1 | 2/2010 | Markovic |
| 2010/0092489 A1 | 4/2010 | Van De Winkel et al. |
| 2010/0112077 A1 | 5/2010 | Desai et al. |
| 2010/0172835 A1 | 7/2010 | Ruoslahti |
| 2010/0260679 A1 | 10/2010 | Shachar et al. |
| 2010/0311679 A1 | 12/2010 | Olson et al. |
| 2011/0014117 A1 | 1/2011 | Wang et al. |
| 2011/0076273 A1 | 3/2011 | Adler et al. |
| 2011/0097340 A1 | 4/2011 | Ramachandra et al. |
| 2011/0104143 A1 | 5/2011 | Buchsbaum et al. |
| 2011/0150902 A1 | 6/2011 | Markovic |
| 2011/0262525 A1 | 10/2011 | Wang et al. |
| 2012/0263739 A1 | 10/2012 | Langer et al. |
| 2012/0315273 A1 | 12/2012 | Markovic |
| 2013/0028895 A1 | 1/2013 | Wulf |
| 2013/0071403 A1 | 3/2013 | Rolland et al. |
| 2013/0149238 A1 | 6/2013 | Kavlie et al. |
| 2013/0164816 A1 | 6/2013 | Chang et al. |
| 2014/0056909 A1 | 2/2014 | Markovic |
| 2014/0155344 A1 | 6/2014 | Desai et al. |
| 2014/0161819 A1 | 6/2014 | Hann et al. |
| 2014/0178486 A1 | 6/2014 | Markovic et al. |
| 2014/0302017 A1 | 10/2014 | Markovic |
| 2014/0314774 A1 | 10/2014 | Zhou et al. |
| 2015/0050356 A1 | 2/2015 | Desai et al. |
| 2015/0246122 A1 | 9/2015 | Markovic et al. |
| 2016/0095942 A1 | 4/2016 | Markovic et al. |
| 2016/0184229 A1 | 6/2016 | Markovic et al. |
| 2016/0184452 A1 | 6/2016 | Markovic et al. |
| 2016/0184453 A1 | 6/2016 | Markovic et al. |
| 2016/0235860 A1 | 8/2016 | Markovic et al. |
| 2016/0250351 A1 | 9/2016 | Markovic et al. |
| 2016/0256431 A1 | 9/2016 | Markovic et al. |
| 2016/0263241 A1 | 9/2016 | Markovc et al. |
| 2016/0310610 A1 | 10/2016 | Markovic et al. |
| 2016/0324964 A1 | 11/2016 | Markovic et al. |
| 2016/0338961 A1 | 11/2016 | Markovic et al. |
| 2016/0339118 A1 | 11/2016 | Markovic et al. |
| 2017/0021023 A1 | 1/2017 | Dikstein |
| 2017/0021032 A1 | 1/2017 | Markovic et al. |
| 2017/0021034 A1 | 1/2017 | Markovic et al. |
| 2017/0071897 A1 | 3/2017 | Markovic et al. |
| 2017/0095574 A1 | 4/2017 | Swiss et al. |
| 2017/0100492 A1 | 4/2017 | Markovic et al. |
| 2017/0106087 A1 | 4/2017 | Markovic et al. |
| 2017/0128408 A1 | 5/2017 | Markovic et al. |
| 2017/0128583 A1 | 5/2017 | Markovic et al. |
| 2017/0128584 A1 | 5/2017 | Markovic et al. |
| 2017/0128585 A1 | 5/2017 | Markovic et al. |
| 2017/0128586 A1 | 5/2017 | Markovic et al. |
| 2017/0128587 A1 | 5/2017 | Markovic et al. |
| 2017/0128588 A1 | 5/2017 | Markovic et al. |
| 2017/0182174 A1 | 6/2017 | Markovic et al. |
| 2017/0182175 A1 | 6/2017 | Markovic et al. |
| 2017/0182180 A1 | 6/2017 | Markovic et al. |
| 2017/0182183 A1 | 6/2017 | Markovic et al. |
| 2017/0182184 A1 | 6/2017 | Markovic et al. |
| 2017/0182185 A1 | 6/2017 | Markovic et al. |
| 2017/0182186 A1 | 6/2017 | Markovic et al. |
| 2017/0182187 A1 | 6/2017 | Markovic et al. |
| 2017/0195832 A1 | 7/2017 | Markovic et al. |
| 2017/0196831 A1 | 7/2017 | Markovic et al. |
| 2017/0196833 A1 | 7/2017 | Markovic et al. |
| 2017/0216453 A1 | 8/2017 | Markovic et al. |
| 2017/0232102 A1 | 8/2017 | Markovic et al. |
| 2017/0291952 A1 | 10/2017 | Markovic et al. |
| 2018/0235886 A1 | 8/2018 | Markovic et al. |
| 2019/0022188 A1 | 1/2019 | Markovic |
| 2019/0038761 A1 | 2/2019 | Markovic et al. |
| 2019/0184032 A1 | 6/2019 | Markovic et al. |
| 2019/0201546 A1 | 7/2019 | Markovic et al. |
| 2019/0202916 A1 | 7/2019 | Markovic et al. |
| 2019/0216944 A1 | 7/2019 | Markovic et al. |
| 2020/0237907 A1 | 7/2020 | Swiss et al. |
| 2020/0268884 A1 | 8/2020 | Markovic et al. |
| 2020/0308294 A1 | 10/2020 | Markovic et al. |

FOREIGN PATENT DOCUMENTS

| | | |
|---|---|---|
| EP | 3533870 | 9/2019 |
| JP | S60146833 | 8/1985 |
| JP | S6178731 | 4/1986 |
| JP | H04504253 | 7/1992 |
| JP | 2001072589 | 3/2001 |
| JP | 2012522809 | 9/2012 |
| KR | 1020090078330 | 7/2009 |
| RU | 2011133819 | 2/2013 |
| RU | 2505315 C2 | 1/2014 |
| WO | 89/10398 | 11/1989 |
| WO | 97/49390 A1 | 12/1997 |
| WO | 99/00113 | 1/1999 |
| WO | 99/51248 | 10/1999 |
| WO | 2004/022097 | 3/2004 |
| WO | 2004/096224 | 11/2004 |
| WO | 2006/034455 | 3/2006 |
| WO | 2006/089290 | 8/2006 |
| WO | 2007/027819 | 3/2007 |
| WO | 2007/027941 | 3/2007 |
| WO | 2008/047272 | 4/2008 |
| WO | 2008/057561 | 5/2008 |
| WO | 2008/057562 | 5/2008 |
| WO | 2008076373 A1 | 6/2008 |

(56) References Cited

FOREIGN PATENT DOCUMENTS

| | | |
|---|---|---|
| WO | 2008/112987 | 9/2008 |
| WO | 2009/043153 | 4/2009 |
| WO | 2009/055343 | 4/2009 |
| WO | 2010/003057 | 1/2010 |
| WO | 2010/017216 | 2/2010 |
| WO | 2010/118365 | 10/2010 |
| WO | 2010/124009 | 10/2010 |
| WO | 2010/136492 | 12/2010 |
| WO | 2012/048223 | 4/2012 |
| WO | 2012/088388 | 6/2012 |
| WO | 2012/154861 A2 | 11/2012 |
| WO | 2014/009774 | 1/2014 |
| WO | 2014/037422 | 3/2014 |
| WO | 2014/055415 | 4/2014 |
| WO | 2014/105644 | 7/2014 |
| WO | 2014/123612 | 8/2014 |
| WO | 2015/048520 | 4/2015 |
| WO | 2015/191969 | 12/2015 |
| WO | 2015/195476 | 12/2015 |
| WO | 2016/057554 | 4/2016 |
| WO | 2016/059220 | 4/2016 |
| WO | 2016/089873 | 6/2016 |
| WO | 2017/031368 | 2/2017 |
| WO | 2017/062063 | 4/2017 |
| WO | 2017/120501 | 7/2017 |
| WO | 2017/139698 | 8/2017 |
| WO | 2017/165440 | 8/2017 |
| WO | 2017/165439 | 9/2017 |
| WO | 2017/176265 | 10/2017 |
| WO | 2018/027205 | 2/2018 |
| WO | 2016/045238 | 3/2018 |
| WO | 2018/045239 | 3/2018 |
| WO | 2018/048815 | 3/2018 |
| WO | 2018/048816 | 3/2018 |
| WO | 2018/048958 | 3/2018 |

OTHER PUBLICATIONS

U.S. Appl. No. 15/460,699; office action dated Aug. 28, 2019.
U.S. Appl. No. 15/461,288; office action dated Aug. 28, 2019.
U.S. Appl. No. 15/752,155; office action dated Sep. 25, 2019.
Cirstoiu-Hapca et al. "Benefit of anti-HER2-coated paclitaxel-loaded imimuno-nanpoarticles in the treatment of disseminated ovarian cancer: Therapeutic efficacy and biodistribution in mice", Journal of Controlled Release 144:324-331 (2010).
Liu et al. "Freeze-Drying of Proteins". In: Walkers W., Odenhof H. (eds) Cryopreservation and Freeze-Drying Protocols. Methods in Molecular Biology (Methods and Protocols), vol. 1257. Springer, New York, NY; published online Nov. 14, 2014.
European Application No. 17771006.8, Extended European Search Report dated Oct. 10, 2019.
European Application No. 17771005.0, Extended European Search Report dated Oct. 17, 2019.
"Concurrent Infusions"; J Oncol Pract., 4(4): 171, Jul. 2008.
Abraxane® for Injectable Suspension (paclitaxel protein-bound particles for injectable suspension) (albumin-bound), [drug label], 22 pages, Sep. 2009.
Adams et al., "(P2-11-01) Safety and clinical activity of atezolizumab (anti-PDL1) in combinatlon with nab-paclitaxel in patients with metastatic triple-negative breast cancer", 2015, XP002775314, 2015 San Antonio Breast Cancer Symposium, URL:http:/sabcs.org/portals/sabcs2016/documents/sabcs-2015-abstracts.pdf?v=5.
Adams et al., "Phase Ib trial of atezolizumab in combination with nab-paclitaxel in patients with metastatic triple-negative breast cancer (mTNBC)" Journal of Clinical Oncology col. 34, No. 15. May 1, 2016, 4 pages.
Agarwal et al., "Flow Cytometric analysis of ThI and Th2 cytokines in PBMCs as a parameter of immunological dysfunction in patlenis of Superficial Transitional cell carcinoma of bladder", Cancer Immunol. Immunother., 2006, S5(6):734-743.

Agarwala et al., "Randomized phase III study of paclitaxel plus carboplatin with or without sorafenib as second-line treatment in patients with advanced melanoma", J. Clin. Oncol. 2007, 25(18S):8510 (Abstract).
Allen "Ligand-targeted therapeutics in anticancer therapy, Cancer", Oct. 2002, 2(10), pp. 750-763.
Alley et al., "Contribution of Linker Stability to the Activities of Anticancer Immunoconjugates", Bioconjugate Chem., 2008, 19(3), pp. 759-765.
Anonymous, "A Phase II, multicenter randomized, double-blind placebo-controlled trial evaluating the efficacy and salety of bevaoizumab in combination with carboplatin and paclitaxel chemotherapy for the first-line treatment of patients with metastatic melanoma", U.S. National Institutes of Health, 2007, 3 pages.
Anonymous, "A Phase III, Multicenter, Randomized Placebo-Controlled Study of Atezolizumab (Anti-PD-L1 Antibody) in Combination with Nab Paclitaxel Compared with Placebo with Nab Paclitaxel for Patients with Previously Untreated Metastatic Triple Negative Breast Cancer", ClinicalTrials.gov, Apr. 21, 2015, 1 page.
Anonymous, "Atezolizumab Plus Abraxane Promising New Treatment for Triple-Negative Breast Cancer", UNM Comprehensive Cancer Center, Jan. 7, 2016, pp. 1-2.
Anonymous, "Phase II trial of carboplatin, weekly paclitaxel and biweekly bevacizumab in patients with unresectable stage IV melanoma", U.S. National Institutes of Health, 2007, 4 pages.
Anonymous, "A Study of Bevacizumab With Carboplatin and Pactitaxel Chemotherapy for the First-Line Treatment of Patients With Metastatic Melanoma (BEAM);" ClinicalTrials.gov [online]. Retrieved from the Internet: URL: https://clinicaltrials.gov/archive/NCT00434252/200703 12. dated Mar. 12, 2007, 3 pages.
U.S. Appl. No. 14/116,619, office action dated Feb. 4, 2015.
U.S. Appl. No. 14/116,619, office action dated Apr. 28, 2016.
U.S. Appl. No. 14/116,619, office action dated Sep. 10, 2015.
U.S. Appl. No. 14/432,979, office action dated May 16, 2018.
U.S. Appl. No. 14/432,979, office action dated Jun. 30, 2016.
U.S. Appl. No. 14/432,979, office action dated Oct. 4, 2017.
U.S. Appl. No. 14/432,979, office action dated Dec. 15, 2016.
U.S. Appl. No. 14/882,327, office action dated May 2, 2016.
U.S. Appl. No. 15/030,567, office action dated Sep. 7, 2016.
U.S. Appl. No. 15/030,568, office action dated May 25, 2017.
U.S. Appl. No. 15/030,568, office action dated Jun. 18, 2018.
U.S. Appl. No. 15/030,568, office action dated Dec. 1, 2017.
U.S. Appl. No. 15/052,336, office action dated Feb. 9, 2018.
U.S. Appl. No. 15/052,336, office action dated Sep. 4, 2018.
U.S. Appl. No. 15/052,623, office action dated Feb. 9, 2018.
U.S. Appl. No. 15/052,623, office action dated May 19, 2017.
U.S. Appl. No. 15/052,823, office action dated Jul. 9, 2018.
U.S. Appl. No. 15/052,623, office action dated Nov. 25, 2016.
U.S. Appl. No. 15/060,967, office action dated Aug. 2, 2016.
U.S. Appl. No. 15/064,396, office action dated Aug. 9, 2016.
U.S. Appl. No. 15/092,403, office action dated Apr. 2, 2018.
U.S. Appl. No. 15/092,403, office action dated Oct. 4, 2018.
U.S. Appl. No. 15/092,433, office action dated Mar. 21, 2018.
U.S. Appl. No. 15/092,433, office action dated Aug. 10, 2018.
U.S. Appl. No. 15/092,433, office action dated Oct. 11, 2017.
U.S. Appl. No. 15/187,672, office action dated May 31, 2018.
U.S. Appl. No. 15/202,115, office action dated Jan. 20, 2017.
U.S. Appl. No. 15/202,115, office action dated Sep. 26, 2016.
U.S. Appl. No. 15/225,428, office action dated Aug. 14, 2018.
U.S. Appl. No. 15/225,428, office action dated Dec. 20, 2017.
U.S. Appl. No. 15/225,504, office action dated Apr. 4, 2017.
U.S. Appl. No. 15/225,504, office action dated Aug. 1, 2018.
U.S. Appl. No. 15/225,504, office action dated Nov. 9, 2016.
U.S. Appl. No. 15/225,542, office action dated Apr. 4, 2017.
U.S. Appl. No. 15/225,542, office action dated Nov. 22, 2016.
U.S. Appl. No. 15/286,006, office action dated Jan. 9, 2017.
U.S. Appl. No. 15/286,006, office action dated Jan. 18, 2018.
U.S. Appl. No. 15/286,006, office action dated May 16, 2017.
U.S. Appl. No. 15/286,024, office action dated Jan. 6, 2017.
U.S. Appl. No. 15/286,024, office action dated May 19, 2017.
U.S. Appl. No. 15/331,754; office action dated Oct. 11, 2018.
U.S. Appl. No. 15/359,569, office action dated Feb. 22, 2017.
U.S. Appl. No. 15/359,569, office action dated Jun. 23, 2017.

(56) References Cited

OTHER PUBLICATIONS

U.S. Appl. No. 15/359,569, office action dated Jul. 12, 2018.
U.S. Appl. No. 15/412,554, office action dated Sep. 27, 2018.
U.S. Appl. No. 15/412,564, office action dated Jul. 10, 2018.
U.S. Appl. No. 15/412,596, office action dated Sep. 4, 2018.
U.S. Appl. No. 15/412,610, office action dated Jul. 9, 2018.
U.S. Appl. No. 15/413,257; office action dated Sep. 25, 2018.
U.S. Appl. No. 15/414,536; office action dated Oct. 11, 2018.
U.S. Appl. No. 15/452,669; office action dated May 5, 2017.
U.S. Appl. No. 15/452,669, office action dated Nov. 16, 2017.
Arakawa et al., "Protein-Solvent Interactions in Pharmaceutical Formulations", Pharm. Res., Mar. 1991, vol. 8, Issue 3, pp. 285-291.
Armitage et al., "New approach to classifying non-Hodgkin's lymphomas: clinical features of the major histologic subtypes. Non-Hodgkin's Lymphoma Classification Project" J Clin Oncol 16, 2780-2795 (1998).
Asadullah et al., "Interleukin-10 therapy—review of a new approach", Pharmarcol Rev., 2003, 55(2):241-269.
Atkins et al., "High-dose recombinant interleukin-2 therapy in patients with metastatic melanoma: long-term survival update", Cancer J Sci Am., 2000, Suppl 6:SII-14.
Atkins, "Interleukin-2: clinical applications", Semin Oncol., 2002, 29(3 Suppl 7):12-27.
Avastin® Bevacizumab, Roche, [drug label], 24 pages, Sep. 2008.
Baba, Oleo Science 10(1):15-18 (Jan. 2010).
Bairagi et al., Albumin: A Versatile Drug Carrier, Austin Therapeutics (Nov. 17, 2015) vol. 2, No. 2, p. 1021 (pp. 1-6).
Balch et al., "The new melanoma staging system", Semin Cutan Med Surg., 2003, 22(1):42-54.
Balch et al., "Update on the melanoma staging system: The importance of sentinel node staging and primary tumor mitotic rate", Journal of Surgical Oncology, Aug. 19, 2011, vol. 104, Issue 4, pp. 379-385.
Bauer et al., "Rituximab, ofatumumab, and other monoclonal anti-CD20 antibodies for chronic lymphocytic leukaemia (Review)," Cochrane Database of Systematic Reviews, Issue 11, 125 pages (copyright 2012).
Baumgartner et al., "Melanoma induces immunosuppression by up-regulating FOXP3(+) regulatory T cells", J Surg Res., 2007, 141(1): 72-77.
Belani et al., "Multicenter, randomized trial for stage IIIB or IV non-small-cell lung cancer using weekly paclitaxel and carboplatin followed by maintenance weekly paclitaxel or observation", J. Clin. Oncol., 2003, 21:2933-2939.
Bird et al., "Single-chain antigen-binding proteins", Science Oct. 1988, 242(4877), pp. 423-426.
Boasberg et al., "Nab-paclitaxel and bevacizumab as first-line therapy in patients with unresectable stage III and IV melanoma", J Clinical Oncology, 2009, 27, No. 15S, abstract #9071.
Boasberg et al., "Phase II trial of nab-paclitaxel and bevacizumab as first-line therapy in patients with unresectable melanoma", Journal of Clinical Oncology, May 20, 2011, vol. 29, No. 15 Supp. 8543.
Bolstad et al., "A comparison of normalization methods for high density oligonucleotide array data based on variance and bias", Bioinformatics, 2003, 19:185-193.
Cao et al., "Response of resistant melanoma to a combination of weekly paclitaxel and bevacizumab", Clin Transl Oncol, 2007, 9:119-120.
Carson et al., "A phase 2 trial of a recombinant humanized monoclonal anti-vascular endothelial growth factor (VEGF) antibody in patients with malignant melanoma", Proceedings of the ASCO vol. 22, No. 2873, General Poster Session, Thirty-Ninth Annual Meeting of the American Society of Clinical Oncology. May 31-Jun. 3, 2003, Chicago, IL, 2 pages.
Celis, "Overlapping human leukocyte antigen class I/II binding peptide vaccine for the treatment of patients with state IV melanoma: evidence of systemic immune dysfunction", Cancer, 2007, 110(1):203-214.
Chapman et al., "Improved Survival with Vemurafenib in Melanoma with BRAF V600E Mutation", The New England Journal of Medicine, Jun. 30, 2011, vol. 364, Issue 26, pp. 2507-2516.
Chisholm et al., "Response to infuenza immunization during treatment for cancer", Arch Dis Child, 2001, 84(6):496-500.
Chong et al., "Combining cancer vaccines with chemotherapy", Expert Opin Pharmacother., 2006, 6(16):2813-2820.
Cleland et al., "The Development of Stable Protein Formulations: A close look at protein aggregation, deamidation, and oxidation", Therapeutic Drug Carrier Systems, 1993, 10(4), pp. 307-377.
Colman, "Effects of amino acid sequence changes on antibody-antigen interactions," Research in Immunology (145(1):33-36, (1994).
Davis, "Affinity separation of antibody-toxin conjugate from albumin-stabilized formulation", Am Biotechnol Lab., 12(4):60-64, Mar. 1994.
Degrasse, "A Single-Stranded DNA Aptamer That Selectively Binds to *Staphylococcus aureus* Enterotoxin B", PLoS One, 2012, 7(3) e33410, pp. 1-7.
Deguchi et al., "Effect of Methotrexate-Monoclonal Anti-Prostatic Acid Phosphatase Antibody Conjugate on Human Prostate Tumor", Cancer Research, Aug. 1986, 46, pp. 3751-3755.
Demirkesen et al., "The correlation of angiogenesis with metastasis in primary cutaneous melanoma: a comparative analysis of microvessel density, expression of vascular endothelial growth factor and basic fibroblastic growth factor", Pathology, 2006, 38:132-137.
Denardo et al., "Inflammation and breast cancer. Balancing immune response: crosstalk between adaptive and innate immune cells during breast cancer progression", Breast Cancer Res., 2007, 9(4):212.
Desai et al., "Enhanced antitumor activity and safety of albumin-bound nab-docetaxel versus polysorbate 80-based docetaxel", Eur. J. Cancer, Suppl.; 18th Symposium on molecular targets and cancer therapeutics; Prague, Czech Republic, Nov. 7-10, 2006, vol. 4, No. 12, Nov. 2006 Nov. 2006, p. 49.
Desai et al., "Increased antitumor activity, intratumor paclitaxel concentrations, and endothelial cell transport of cremophor-free, albumin-bound paclitaxel, ABI-007, compared with cremophor-based paclitaxel", Clin Cancer Res., 2006, 12(4): 1317-24.
Deweers et al., "Daratumumab, a novel therapeutic human CD38 monoclonal antibody, induces killing of multiple myeloma and other hematological tumors", J. Immunol., 186(3): 1840-1848, Feb. 1, 2011.
Dudek et al., "Autologous large multivalent immunogen vaccine in patients with metastatic melanoma and renal cell carcinoma", Am. J. Clin. Oncol., Apr. 1, 2008, 31(2):173-181.
Edison, "MorphoSys," 15 pages (Aug. 8, 2013).
Elbayoumi et al., "Tumor-Targeted Nanomedicines: Enhanced Antitumor Efficacy In vivo of Doxorubicin-Loaded, Long-Circulating Liposomes Modified with Cancer-Specific Monoclonal Antibody", Clin Cancer Res., 2009, 15(6): 1973-1980.
Ellyard et al., "Th2-mediated anti-tumour immunity: friend or foe?", Tissue Antigens, 2007, 70(1):1-11.
Elsadek et al., "Impact of albumin on drug delivery—New applications on the horizon", J of Controlled Release, 2011, 1-25.
Emens et al.: "(OT1-01-06) A phase III randomized trial of atezolizumab in combination with nab-paclitaxel as first line therapy for patienst with metastatic triple-negative breast cancer (mTNBC)", 2015, XP002775313, 2015 San Antonio Breast Cancer Symposium, URL: http://sabcs.org/portals/sabcs2016/documents/sabcs-2015-abstracts.pdf?v=5.
European Application No. 08743903.0, Extended European Search Report dated Jan. 24, 2011.
European Application No. 09774506.1, Extended European Search Report dated Mar. 22, 2012.
European Application No. 12781802.9, Extended European Search Report dated Dec. 18, 2014.
European Application No. 13843209.1, Extended European Search Report dated Sep. 5, 2016.
European Application No. 15806443.6, Extended European Search Report dated Dec. 11, 2017.
European Application No. 15809075.3, Extended European Search Report dated Dec. 21, 2017.
Fabi et al, "Prospective study on nanoparticle albumin-bound paclitaael in advanced breast cancer: clinical results and biological observa-

(56) References Cited

OTHER PUBLICATIONS tions in taxane-pretreated patients", Drug Design, Development and Therapy vol. 9, Nov. 1, 2015, 7 pages.
Ferrara et al., "The biology of VEGF and its receptors", Nat. Med., 2003, 9:669-676.
Flaherty et al., "Final Results of E2603: a double-blind, randomized phase III trial comparing carboplatin (C)/paclitaxel(P) with or without sorafenib(S) in metastatic melanoma", J. Clin Oncol., 2010, 28:15s (suppl: abstr 8511).
Flores et al., "Novel oral taxane therapies: recent Phase I results", Clin. Invest. vol. 3, No. 4, Apr. 1, 2013 (Apr. 1, 2013), pp. 333-341, XP055426571, UK, ISSN: 2041-6792, DOI: 10.4155/cli.13.18.
Folkman, "Angiogenesis in cancer, vascular, rheumatoid and other disease", Nat. Med., 1995, 1, 27-31.
Fricke et al., "Vascular endothelial growth factor-trap overcomes defects in dendritic cell differentiation but does not improve antigen-specific immune responses", Clin. Cancer Res., 2007, 13:4840-4848.
Gabrilovich et al., "Production of vascular endothelial growth factor by human tumors inhibits the functional maturation of dendritic cells", Nat. Med., 1996, 2: 1096-1103.
Gao et al., "In vivo cancer targeting and imaging with semiconductor quantum dots", Nat Biotech, 2004, 22(8):969-976.
Gogas et al., "Chemotherapy for metastatic melanoma: time for a change?", Cancer, 2007, 109(3): 455-464.
Golay et al., "Mechanism of action of therapeutic monoclonal antibodies: promises and pitfalls of in vitro and in vivo assay," Arch. Biochem. Biophys, 526(2):146-153 (2012).
Graells et al., Overproduction of VEGF165 concomitantly expressed with its receptors promotes growth and survival of melanoma cells through MAPK and P13K signaling, J. Invest. Dermatol., 2004, 123:1151-1161.
Gupta et al., "Ofatumumab, the first human anti-CD20 monoclonal antibody for the treatment of B cell hematologic malignancies," Ann. N.Y. Acad. Sci., 1263, pp. 43-56 (Jul. 25, 2012).
Haley et al., "Nanoparticles for drug delivery in cancer treatment", Urol. Oncol.: Seminars and Origianl Invest., 2008, 26:57-64.
Hamilton et al, "Nab-Paclitaxel/Bevacizumab/Carboplatin Chemotherapy in First-Line Triple Negative Metastatic Breast Cancer", Clinical Breast Cancer, vol. 13, No. 6, Dec. 1, 2013, 6 pages.
Hara, "What is anti-HER2 antibody tubulin polymerization inhibitor complex T-DM1?," Pharm. Monthy 56(5):734-739 (May 2014).
Harlow et al., Antibodies: A Laboratory Manual, Cold Spring Harbor Laboratory, New York 1988 (9 pages).
Hassan et al: "Comparison of Different Crosslinking Methods for Preparation of Docetaxel-loaded Albumin Nanoparticles", Iranian Journal of Pharmaceutical Research, vol. 14, No. 2, Apr. 2015 (Apr. 2015), pp. 385-394.
Hauschild et al., "Individualized therapy of disseminated cancer using malignant melanoma as a model", Cancer and Metastasis Reviews, 2006, 25(2): 253-256.
Hauschild et al., "Results of a Phase III, Randomized, Placebo-Controlled Study of Sorafenib in Combination with Carboplatin and Paclitaxel as Second-Line Treatment in Patients with Unresectable Stage III or Stage IV Melanoma", Journal of Clinical Oncology, Jun. 10, 2009, vol. 27, No. 17, pp. 2823-2830.
Hegde et al. "Predictive Impact of Circulating Vascular Endothelial Growth Factor in Four Phase III Trials Evaluating Bevacizumab," Clinical Cancer Research, Feb. 15, 2013 (Feb. 15, 2013) vol. 19, pp. 929-937.
Hersh et al., "A Phase 2 Clinical Trial of nab-Paclitaxel in Previously Treated and Chemotherapy-Naïve Patients With Metastatic Melanoma", Cancer, Jan. 1, 2010, 116:155, pp. 155-163.
Hersh et al., "A randomized, controlled phase III trial of nab-Paclitaxel versus dacarbazine in chemotherapy-naïve patients with metastatic melanoma", Ann Oncol, 2015, epub Sep. 26, 2015.
Hersh et al., "Open-label, multicenter, phases II trial of ABI-007 in previously treated and previously untreated patients with metastatic malignant melanoma", J. Clin. Oncol., 2005, 23(16S):7558 (Abstract).

Hobbs et al., "Regulation of Transport pathways in tumor vessels: role of tumor type and microenvironment", Proc Natl Acad Sci USA, Apr. 1998, 95, pp. 4607-4612.
Hodi et al., "Improved survival with ipilimumab in patients with metastatic melanoma", The New England Journal of Medicine, Aug. 19, 2010, vol. 363, No. 8, pp. 711-723.
Hodi et al., "Phase II study of paclitaxel and carboplatin for malignant melanoma", Am. J. Clin. Oncol., 2002, 25:283-286.
Hood et al., Immunology, 1984, Benjamin, N.Y., 2nd edition.
Huncharek et al., "Single-agent DTIC versus combination chemotherapy with or without immunotherapy in metastatic melanoma: a meta-analysis of 3273 patients from 20 randomized trials", Melanoma Research, 11:75-81 (2001).
Hunkapiller et al., "Immunology: The growing immunoglobulin gene superfamily", Nature, Sep. 1986, 323; pp. 15-16.
Huston et al., "Protein engineering of antibody binding sites: Recovery of specific activity in an anti-digoxin single-chain Fv analogue produced in *Escherichia coli*", Proc. Natl. Acad. Sci. USA, Aug. 1988, vol. 85, pp. 5879-5883.
Ibrahim et al., "Phase I and Pharmacokinetic Study of ABI-007, a Cremophor-free, Protein-stabilized, Nanoparticle Formulation of Paclitaxel", Clinical Cancer Research, May 2002, vol. 8, pp. 1038-1044.
Inagaki et al., "Clinical significance of serum Th1-, Th2- and regulatory T cells-associated cytokines in adult T-cell leukemia/lymphoma: High Interleukin-5 and -10 levels are significant unfavorable prognostic factors", Int. J. Cancer, 2006, 118(12):3054-3061.
Inman, "Atezolizumab/Nab-Paclitaxel Combo Shows High Response Rates in TNBC", OneLive, Dec. 10, 2015, 4 pages.
International Preliminary Report on Patentability for Application No. PCT/US2008/057025, dated Sep. 15, 2009.
International Preliminary Report on Patentability for Application No. PCT/US2009/049511, dated Jan. 5, 2011.
International Preliminary Report on Patentability for Application No. PCT/US2012/037137, dated Nov. 12, 2013.
International Preliminary Report on Patentability for Application No. PCT/US2013/062638, dated Apr. 16, 2015.
International Preliminary Report on Patentability for Application No. PCT/US2015/035505 dated Dec. 22, 2016.
International Preliminary Report on Patentability for Application No. PCT/US2015/035515, dated Dec. 29, 2016.
International Preliminary Report on Patentability for Application No. PCT/US2015/054295, dated Oct. 13, 2016.
International Preliminary Report on Patentability for Application No. PCT/US2016/026270, dated Oct. 18, 2018.
International Preliminary Report on Patentability for Application No. PCT/US2017/012580, dated Jul. 19, 2018.
International Preliminary Report on Patentability for Application No. PCT/US2016/026267, dated Apr. 10, 2018.
International Preliminary Report on Patentability for Application No. PCT/US2017/017553, dated Aug. 23, 2018.
International Search Report and Written Opinion for Application No. PCT/US2008/057025, dated Jul. 1, 2008.
International Search Report and Written Opinion for Application No. PCT/US2009/049511, dated Feb. 2, 2010.
International Search Report and Written Opinion for Application No. PCT/US2012/037137, dated Sep. 28, 2012.
International Search Report and Written Opinion for Application No. PCT/US2013/062638, dated Jan. 23, 2014.
International Search Report and Written Opinion for Application No. PCT/US2015/035505, dated Nov. 24, 2015.
International Search Report and Written Opinion for Application No. PCT/US2015/035515, dated Sep. 21, 2015.
International Search Report and Written Opinion for Application No. PCT/US2015/054295, dated Jan. 25, 2016.
International Search Report and Written Opinion for Application No. PCT/US2016/026267, dated Jul. 12, 2016.
International Search Report and Written Opinion for Application No. PCT/US2016/026270, dated Oct. 12, 2017.
International Search Report and Written Opinion for Application No. PCT/US2016/047641, dated Oct. 31, 2016.

(56) References Cited

OTHER PUBLICATIONS

International Search Report and Written Opinion for Application No. PCT/US2017/012580, dated Mar. 17, 2017.
International Search Report and Written Opinion for Application No. PCT/US2017/017553, dated Feb. 10, 2017.
International Search Report and Written Opinion for Application No. PCT/US2017/045643, dated Oct. 25, 2017.
International Search Report and Written Opinion for Application No. PCT/US2017/049745, dated Dec. 15, 2017.
International Search Report and Written Opinion for Application No. PCT/US2017/049746, dated Nov. 27, 2017.
International Search Report and Written Opinion for Application No. PCT/US2017/050134, dated Nov. 16, 2017.
International Search Report and Written Opinion for Application No. PCT/US2017/050137, dated Nov. 27, 2017.
International Search Report and Written Opinion for Application No. PCT/US2017/050355, dated Jan. 30, 2018.
Jaime et al., "Paclitaxel antibody conjugates and trehalose for preserving the immunological activity after freeze-drying," Curr Med Chem, 2004, 11(4):439-46 Abstract Only.
Jain et al., "Delivering nanomedicine to solid tumors", Nature Reviews Clinical Oncology, Nov. 2010, 7, pp. 653-664.
Jain et al., "Normalizing tumor vasculature with anti-angiogenic therapy: a new paradigm for combination therapy," Nat. Med. 7(9):987-989 (2001).
Jain, "Normalization of tumor vasculature: an emerging concept in antiangiogenic therapy," Science 307(5706):58-62 (2005).
Jazirehi et al., "Rituximab (anti-CD20) selectively modifies Bcl-xl and apoptosis protease activating factor-1 (Apaf-1) expression and sensitizes human non-Hodgkin's lymphoma B cell lines to paclitaxel-induced apoptosis," Mol. Cancer Ther. 2(11):1183-93 (2003).
Jiang et al., "Regulation of Immune Responses by T Cells", N Engl J Med., 2006, 354(11): 1166-1176.
Jin et al., "Paclitaxel-loaded nanoparticles decorated with anti-CD133 antibody: a targeted therapy for liver cancer stem cells," J. Nanopart. Res. 2014, 16:2157 (2014).
Jin et al: "Docetaxel-loaded PEG-albumin nanoparticles with improved antitumor efficiency against non-small cell lung cancer", Oncology Reports vol. 36, No. 2, Aug. 8, 2016 (Aug. 8, 2016), pp. 871-876, XP055425487, ISSN: 1021-335X, DOI: 10.3892/or.2016.4863.
Julien et al, "Utilization of monoclonal antibody-targeted nanomaterials in the treatment of cancer", 2011, MAbs, 3:467-478.
Kamat et al., "Metronomic chemotherapy enhances the efficacy of antivascular therapy in ovarian cancer", Cancer Res., 2007, 67(1):281-288.
Kawai et al., "VEGF 121 promotes lymphangiogenesis in the sentinel lymph nodes of non-small cell lung carcinoma patients", Lung Cancer, 2008, 59(1):41-47.
Kelly et al. "Shape-Specific, Monodisperse Nano-Molding of Protein Particles," J. Am. Chem. Soc. 130:5438-5439 (2008).
Kikuchi et al., "Vascular endothelial growth factor and dendritic cells in human squamous cell carcinoma of the oral cavity", Anticancer Res., 2006, 26(3A):1833-1848.
Kim et al., "A dual target-directed agent against interleukin-6 receptor and tumor necrosis factor a ameliorates experimental arthritis", Scientific Rep. 6:20150 (2016).
Kim et al., "BEAM: A Randomized Phase II Study Evaluating the Activity of Bevacizumab in Combination with Carboplatin Plus Paclitaxel in Patients with Previously Untreated Advanced Melanoma", Journal of Clinical Oncoloy: official journal of the American Society of Clinical Oncology, Jan. 1, 2012, vol. 30, No. 1, pp. 34-41.
Kirkwood et al., "A pooled analysis of eastern cooperative oncology group and intergroup trials of adjuvant high-dose interferon for melanoma", Clin Cancer Res., 2004, 10(5):1670-1677.
Kondejewski et al., "Synthesis and characterization of carbohydrate-linked murine monoclonal antibody K20-human serum albumin conjugates", Bioconjug Chem., 5(6):602-611, Nov.-Dec. 1994.
Korman et al., "Tumor immunotherapy: preclinical and clinical activity of anti-CTLA4 antibodies", Curr Opin Invest Drugs, 2005, 6(6):582-591.
Kottschade et al., "A Phase II Trial of Nab-Paclitaxel (ABI-007) and Carboplatin in Patients with Unresectable Stage IV Melanoma", Cancer, Apr. 15, 2011, 117(8), pp. 1704-1710.
Kottschade et al., "A Randomized Phase 2 Study of Temozolomide and Bevacizumab or nab-Paclitaxel, Carboplatin, and Bevacizumab in Patients with Unresectable Stage IV Melanoma",Cancer, 2013, vol. 119, Issue 3, pp. 585-592.
Kratz et al., "Serum proteins as drug carriers of anticancer agents: a review", Drug Deliv., 5(4):281-299, 1998.
Kratz, "Albumin as a drug carrier: design of prodrugs, drug conjugates and nanoparticles", J Control Release, 132(3):171-183, Epub May 17, 2008.
Kukowska-Latallo et al., "Nanoparticle Targeting of Anticancer Drug Improves Therapeutic Response in Animal Model of Human Epithelial Cancer", Cancer Res, 2005, 65(12):5317-5324.
Kumar et al., ThI/Th2 cytokine imbalance in meningioma, anaplastic astrocytoma and glioblastoma multiforme patients, Oncol. Ren., 2006, 15(6):1513-1516.
Lanzavecchia et al., "The use of hybrid hybridomas to target human cytotoxic T lymphocytes", Eur. J. Immunol., 1987, 17, pp. 105-111.
Lau et al., "Is inhibition of cancer angiogenesis and growth by paclitaxel schedule dependent?", Anti-Cancer Drugs, 2004, 15:871-875.
Lee et al., "The co-delivery of paclitaxel and Herceptin using cationic micellar nanoparticles", Biomaterials vol. 30, No. 5, Feb. 1, 2009, pp. 919-927.
Lei et al., "Comparing cellular uptake and cytotoxicity of targeted drug carriers in cancer cell lines with different drug resistance mechanisms", Nanomed: Nanotech, Biol, and Med., 2011, 7:324-332.
Lev et al., "Dacarbazine causes transcriptional up-regulation of interleukin 8 and vascular endothelial growth factor in melanoma cells: a possible escape mechanism from chemotherapy", Mol. Cancer Ther., 2003, 2:753-763.
Lev et al., "Exposure of melanoma cells to dacarbezine results in enhanced tumor growth and metastasis in vivo", J. Clin. Oncol., 2004, 22:2092-2100.
Liang et al., "IFN-alpha regulates NK cell cytotoxicity through STAT1 pathway," Cytokine, Aug. 13, 2003 (Aug. 13, 2013), vol. 23, pp. 190-199.
Lundin et al., "Phase 2 study of alemtuzumab (anti-CD52 monoclonal antibody) in patients with advanced mycosis fungoides/Sezary syndrome", Blood (2003) vol. 101, No. 11, pp. 4267-4272.
Makridis, et al., "MHC class I and II antigen expression and interferon ? treatment of human midgut carcinoid tumors," World Journal of Surgery, Aug. 1, 1993 (Aug. 1, 1993), vol. 16, Iss. 4, pp. 481-486.
Marcoval et al., "Angiogenesis and malignant melanoma. Angiogenesis is related to the development of vertical (tumorigenic) growth phase", J. Cutan. Pathol. 1997, 24:212-218.
Markovic et al., "A phase II study of ABT-510 (thrombospondin-1 analog) for the treatment of metastatic melanoma", Am. J. Clin. Oncol., 2007, 30(3):303-309.
Markovic et al., "A reproducible method for the enumeration of functional ( cytokine producing) versus non-functional peptide-specific cytotoxic T lymphocytes in human peripheral blood", Clin. Exo. Immunol., 2006, 145:438-447.
Markovic et al., "Peptide vaccination of patients with metastatic melanoma: improved clinical outcome in patients demonstrating effective immunization", Am J Clin Oncol., 2006, 29(4):352-360.
Matejtschuk, "Lyophilization of Proteins", Methods in Molecular Biology, Cryopreservation and Freeze-Drying Protocols, Second Edition, Edited by: J.G. Day and G.N. Stacey, Humana Press Inc., Totowa, NJ, 2007, vol. 368, pp. 59-72.
Matsuda et al., Preoperative oral immune-enhancing nutritional supplementation corrects TH1/TH2 imbalance in patients undergoing elective surgery for colorectal cancer, Dis. Colon Rectum, 2006, 49(4):507-516.
Mayo Clinic, "Paclitaxel Albumin-Stabilized Nanoparticle Formulation and Bevacizumab in Treating Patients With Stage IV Melanoma That Cannot Be Removed by Surgery", Dec. 19, 2013, ClinicalTrials.gov., URL: https://www.clinicaltrials.gov/ct2/show/NCT02020707 (Four (4) pages).

(56) References Cited

OTHER PUBLICATIONS

McElroy et al., "Imaging of Primary and Metastatic Pancreatic Cancer Using a Fluorophore-Coniugated Anti-CA19-9 Antibody for Surgical Navigation", World J Surg., 2008, 32: 1057-1066.

Meadows et al. "Anti-VEGF Therapies in the Clinic," Cold Spring Harbor Perspectives in Medicine, Oct. 1, 2012 (Oct. 1, 2012), vol. 2, pp. 1-27.

Melcher, "Recommendations for influenza and pneumococcal vaccinations in people receiving chemotherapy", Clin Oncol (R Coll Radion). 2005, 17(1): 12-15.

Merchan et al., "Increased endothelial uptake of paclitaxel as a potential mechanism for its antiangiogenic effects: potentiation by Cox-2 inhibition", Int. J. Cancer, 2005, 113, pp. 490-498.

Mezzaroba et al., "New potential therapeutic approach for the treatment of B-Cell malignancies using chlorambucil/Hydroxychloroquine-Loaded Anti-CD20 Nanoparticles". Sep. 2013, PLoS ONE vol. No. 8. Issue 9 pp. 1-10, e74216.

Middleton et al., "Randomized phase III study of temozolomide versus dacarbazine in the treatment of patients with advanced metastatic malignant melanoma", J. Clin. Oncol., 2000, 18, pp. 158-166.

Miller et al., "Paclitaxel plus Bevacizumab versus Paclitaxel Alone for Metastatic Breast Cancer," N Engl. J Med., (2007) vol. 357:2666-2676.

Mimura et al., Vascular endothelial growth factor inhibits the function of human mature dendritic cells mediated by VEGF receptor-2, Cancer Immunol Immunother., 2007, 58(6). pp. 761-770.

Mirtsching et al., "A Phase II Study of Weekly Nanoparticle Albumin-Bound Paclitaxel With or Without Trastuzumab in Metastatic Breast Cancer", Clinical Breast Cancer, 2011, 11(2):121-128.

Mocellin et al., "Cytokines and immune response in the tumor microenvironment", J Immunother., 2001, 24(5), pp. 392-407.

Motl, "Bevacizumab in combination chemotherapy for colorectal and other cancers", Am. J. Health-Svst. Pharm 2005. 62, pp. 1021-1032.

Mustacchi et al, "The role of taxanes in triple-negative breast cancer: literature review", Drug Design, Development and Therapy, vol. 9, Aug. 5, 2015, 16 pages.

Nahleh et al, "Swog S0800 (NCI CDR0000636131): addition of bevacizumab to neoadjuvant nab-paclitaxel with dose-dense doxorubicin and cyclophosphamide improves pathologic complete response (pCR) rates in inflammatory or locally advanced breast cancer", Breast Cancer Research and Treatment, vol. 158, No. 3 Jul. 8, 2016, 12 pages.

Nevala et al, "Abstract B77: Targeted nano-immune conjugates to melanoma: Preclinical testing of bevacizumab targeted nab-paclitaxel", Cancer Immunology Research, vol. 3, Oct. 1, 2015, 3 pages.

Nevala et al, "Antibody-targeted paclitaxel loaded nanoparticles for the treatment of CD20 B-cell lymphoma", Scientific Reports, vol. 7, Apr. 5, 2017, 9 pages.

Nevala et al, "Antibody-Targeted Chemotherapy for the Treatment of Melanoma", Cancer Research, vol. 76, No. 13, Jul. 1, 2016, pp. 3954-3964.

Nevala et al, "Targeted nano-immune conjugates to melanoma: Preclinical testing of bevacizumab targeted nab-paclitaxel", Proceedings of the AACR Special Conference: Tumor Immunology and Immunotherapy: A New Chapter, Dec. 1, 2014, 2 pages.

Ng et al., "Influence of formulation vehicle on metronomic taxane chemotherapy: albumin-bound versus cremophor EL-based pactlitaxel", Clin. Cancer Res., 2006, 12, pp. 4331-4338.

Ng et al., "Taxane-mediated antiangiogenesis in vitro: influence of formulation vehicles and binding proteins", Cancer Res., 2004, 64, pp. 821-824.

Nilvebrant et al., "The Albumin-Binding Domain as a Scaffold for Protein Engineering", Computational and Structural Biotechnology Journal, Mar. 2013, vol. 6, Issue 7, e201303099, http://dx.doi.org/10.5936/csbj.201303099.

Nishida et al, english Translation of "Clicial Trials of New Drugs Cytotoxic Effect against Multiple Myeloma with High Expression of a CD38 Antigen and a Human CD38 Monoclonal Antibody Daratumumab:CD38 Antigen", history of Medicine, Sep. 29, 2012, vol. 242, No. 13, pp. 1176-1181.

Oku et al., "Tumor growth modulation by sense and antisense vascular endothelial growth factor gene expression: effects on angiogenesis, vascular permeability, blood volume, blood flow, fluorodeoxyglucose uptake, and proliferation of human melanoma intracerebral xenografts", Cancer Res., 1998, 58, pp. 4185-4192.

Ortaldo et al., "Effects of several species of human leukocyte interferon on cytotoxic activity o fNK cells and monocytes," International Journal of Cancer, Mar. 15, 1983 (Mar. 15, 1983) vol. 31, No. 3, pp. 285-289.

Ouichi, "Antibody delivery—from basics to clinical test—Clinical development of antibody-drug conjugate," Drug Deliv. Sys. 28(5) 424-429 (2013).

Parikh et al., "The vascular endothelial growth factor family and its receptors", Hematol. Oncol. Clin. N. Am., 2004, 18, pp. 951-971.

Park et al., "Anti-HER2 Immunoliposomes: Enhanced Efficacy Attributable to Targeted Delivery", Clin. Cancer Res., 2002, 8, pp. 1172-1181.

Parker et al., "Targeting CLL Cells Using Rituximab-Conjugated Surface Enhanced Raman Scattering (SERS) Gold Nanoparticles," Blood vol. 116, No. 21, Nov. 1, 2010, pp. 1190.

Perez et al., "Phase 2 Trial of Carboplatin, Weekly Paclitaxel, and Biweekly Bevacizumab in Patients with Unresectable Stage IV Melanoma", Cancer, 2009, vol. 115, Issue 1, pp. 119-127.

Petrelli et al., "Targeted Delivery for Breast Cancer Therapy: the History of Nanoparticle-Albumin-Bound Paclitaxel," Expert Opinion on Pharmacotherapy, Jun. 1, 2010 (Jun. 1, 2010), vol. 11, pp. 1413-1432.

Pikal., "Freeze-drying of proteins, Part II: Formulation selection", Biopharm, 1990, 9, pp. 26-30.

Polak et al., "Mechanisms of local immunosuppression in cutaneous melanoma", Br J Cancer, 2007, 96(12), pp. 1879-1887.

Porrata et al., "Early lymphocyte recovery predicts superior survival after autologous hematopoietic stem cell transplantation in multiple myeloma or non-Hodgkin lymphoma", Blood, 2001, 98(3), pp. 579-585.

Porrata et al., "Timely reconstitution of immune competence affects clinical outcome following autologous stem cell transplantation", Clin Exp Med., 2004, 4(2):78-85.

Powell et al., "Adoptive transfer of vaccine-induced peripheral blood mononuclear cells to patients with metastatic melanoma following lymphodepletion", J Immunol., 2006, 177(9), pp. 6527-6539.

Pries et al., "Cytokines in head and neck cancer", Cytokine Growth Factor Rev., 2006, 17(3), pp. 141-146.

Qu Na et al: "Cabazitaxel-loaded human serum albumin nanoparticles as a therapeutic agent against prostate cancer", International Journal of Nanomedicine, vol. 11, Jul. 26, 2016 (Jul. 26, 2016), pp. 3451-3459.

Ranieri et al., "Vascular endothelial growth factor (VEGF) as a target of bevacizumab in cancer: from the biology to the clinic", Curr. Med. Chem., 2006, 13, 1845-1857.

Rao et al., "Combination of Paclitaxel and Carboplatin as Second-Line Therapy for Patients with Metastatic Melanoma", Cancer, Jan. 15, 2006, vol. 106, No. 2, pp. 375-362.

Ribas et al., "Antitumor activity in melanoma and anti-self responses in a phase I trial with the anti-cytotoxic T lymphocyte-associated antigen 4 monoclonal antibody CP-675,206", J Clin Oncol., Dec. 10, 2005, 23(35), pp. 8968-8977.

Rosenberg et al., "Tumor progression can occur despite the induction of very high levels of self/tumor antigen-specific CD8+ T cells in patients with melanoma", J. Immunol., 2005, 175(9), pp. 6169-6176.

Roy et al., "Tumor associated release of interleukin-10 alters the prolactin receptor and down-regulates prolactin responsiveness of immature cortical thymocytes", J Neuroimmunol., 2007, 186(1-2). pp. 112-120.

(56) References Cited

OTHER PUBLICATIONS

Rudikoff et al., "Single amino acid substitution altering antigen-binding specificity," Proc Natl Acad Sci USA 1982 vol. 79 pp. 1979-1983.
Rudnicka et al., "Rituximab causes a polarization of B cells that augments its therapeutic function in NK-cell-mediated antibody-dependent cellular cytotoxicity", Blood, 2013, 121(23):4694-4702.
Sadat et al., "Nano-pharmaceutical Formulations for Targeted Drug Delivery against HER2 in Breast Cancer", Current Cancer Drug Targets, 2015, 15(1):71-86.
Salven et al., "Enhanced expression of vascular endothelial growth factor in metastatic melanoma", Br. J. Cancer, 1997, 76(7), pp. 930-934.
Samaranayake et al., "Modified taxols. 5.1 Reaction of taxol with electrophilic reagents and preparation of a rearranged taxol derivative with tubulin assembly activity", J. Org. Chem., vol. 56, 1991, pp. 5114-5119.
Sandler et al., "Paclitaxel-carboplatin alone or with bevacizumab for non-small-cell lung cancer", N. Engl. J. Med., 2006, 355:2542-2550.
Sato et al., "Intraepithelial CD8+ tumor-infiltrating lymphocytes and a high CD8+/regulatory T cell ratio are associated with favorable prognosis in ovarian cancer", Proc Natl Acad Sci USA, 2005, 102(51):18538-18543.
Schrama et al. "Antibody targeted drugs as cancer therapeutics", Nature Reviews 5:147-159 (2006).
Sester et al., "Differences in CMV-specific T-cell levels and long-term susceptibility to CMV infection after kidney, heart and lung transplantation", Am J Transplant., 5(6):1483-1489, Jun. 2005.
Soda et al., "Latest topics of new medicine Albumin-bound paclitaxel," Mol. Respiratory Dis. 17(1):100-103 (Mar. 1, 2013).
Srivastava et al., "Angiogenesis in cutaneous melanoma: pathogenesis and clinical implications", Microsc. Res. Tech., 2003, 60:208-224.
Stancovski et al., "Mechanistic aspects of the opposing effects of monoclonal antivodies to the ERBB2 receptor on tumor growth," Proc Natl Acad Sci USA, 88: 8691-8695, (1991).
Streit et al., "Angiogenesis, lympangiogenesis, and melanoma metastasis", Oncogene, 2003, 22, pp. 3172-3179.
Taieb et al., "Chemoimmunotherapy of tumors: Cyclophosphamide synergtizes with exoxome based vaccines", J. Immunol., Mar. 1, 2006, 176(5):2722-2729.
Tao et al., "Inhibiting the growth of malignant melanoma by blocking the expression of vascular endothelial growth factor using an RNA interference approach", Br. J. Dermatol., 2005, 153:715-724.
Tas et al., "Circulating serum levels of anglogenic factors and vascular endothelial growth factor receptors 1 and 2 in melanoma patients", Melanoma Res., 2006, 16:405-411.
Terheyden et al., "Anti-vascular endothelial growth factor antibody bevacizumab in conjunction with chemotherapy in metastasizing melanoma", J Cancer Res Clin Oncol, 2007, 133(11), pp. 897-901.
Terui, English Translation of Molecular-Targeted Therapy for Cancer: Progresses and Challenges, "Daratumumab, Antibody Drug against Myeloma", Pharma Med., Nov. 10, 2013, vol. 31, No. 11, pp. 27-30.
Ugurel et al., "Increased serum concentration of angiogenic factors in malignant melanoma patients correlates with tumor progression and survival", J. Clin. Oncol., 2001, 19:577-583.
Vacca et al., "Docetaxel versus paclitaxel for antiangiogenesis", J. Hematother. Stem Cell Res., 2002, 11:103-118.
Varker et al., "A randomized phase 2 trial of bevacizumab with or without daily low-dose interferon alfa-2b in metastatic malignant melanoma", Ann Surg Oncol., 14(8):2367-2376, print Aug. 2007, Epub May 2007.
Vence et al., "Circulating tumor antigen-specific regulatory T cells in patients with metastatic melanoma", Proc Natl Acad Sci USA, 2007, 104(52), pp. 20884-20889.

Volk et al., "Nab-placlitaxel efficacy in the orthotopic model of human breast cancer is significantly enhanced by concurrent anti-vascular endothelial growth factor A therapy," Neoplasma 10(6):613-623 (2008).
Volk-Draper et al, "Novel Model for Baseloid Triple-negative Breast Cancer: Behavior In Vivo and Response to Therapy", vol. 14, No. 10, Oct. 1, 2012, 18 pages.
Wagner et al., "Enhanced drug targeting by attachment of an anti alphav integrin antibody to doxorubicin loaded human serum albumin nanoparticles", Biomaterials., 31(8):2388-2398, Epub Dec. 23, 2009.
Walker et al., "Monitoring immune responses in cancer patients receiving tumor vaccines", Int Rev Immunol., 2003, 22(3-4):283-319.
Wang et al., "Biofunctionalized targeted nanoparticles for therapeutic applications", Expert Opin. Biol. Ther., 2008, 8(8): 1063-1070.
Wang et al., "Paclitaxel at ultra low concentrations inhibits angiogenesis without affecting cellular microtubule assembly", Anti-Cancer Drugs, 2003, vol. 14, Issue 1, pp. 13-19.
Washington University School of Medicine "Phase I/II Study of Abraxane in Recurrent and Refractory Lymphoma", ClinicalTrials.gov, Dec. 6, 2016, 7 pages.
Weber, "Review: anti-CTLA-4 antibody ipilimumab: case studies of clinical response and immune-related adverse events", Oncologist, Jul. 2007, 12(7), pp. 864-872.
Wiernik et al., "Phase I trial of taxol given as a 24-hour infusion every 21 days: responses observed in metastatic melanoma", Journal of Clinical Oncology, Aug. 1987, vol. 5, No. 8, pp. 1232-1239.
Wong et al., "Programmed death-1 blockade enhances expansion and functional capacity of human melanoma antigen-specific CTLs", Int. Immunol., 2007, vol. 19, No. 10, pp. 1223-1234.
Wu et al., "Aptamers: Active Targeting Ligands for Cancer Diagnosis and Therapy", Theranostics, 2015, 5(4):322-344.
Yardley et al., "A pilot study of adjuvant nanoparticle albumin-bound (nab) paclitaxel and cyclophosphamide, with trastuzumab in HER2-positive patients, in the treatment of the early-stage breast cancer", Breast Cancer Res Treat, 2010, 123:471-475.
Yee et al., "Adoptive T cell therapy using antigen-specific CD8+ T cell clones for the treatment of patients with metastatic melanoma: in vivo persistence, migration, and antitumor effect of transferred T cells", Proc Natl Acad Sci USA, 2002, 99(25):16168-16173.
Yu et al., "Interaction between bevacizumab and murine VEGF-A: a reassessment," Invest. Ophthalmol. Visual Sci. 49(2): 522-527, Feb. 2008.
Yuan et al., "Vascular Permeability in a Human Tumor Xenograft: Molecular Size Dependence and Cutoff Size", Cancer Research, Sep. 1, 1995, 55, pp. 3752-3756.
Yuan et al., "Time-dependent vascular regression and permeability changes in established human tumor xenografts induced by an anti-vascular endothelial growth factor/vascular permeability factor antibody," Proc. Natl. Acad. Sci. USA 93(25):14765-14770 (1996).
Zimpfer-Rechner et al., "Randomized phase II study of weekly paclitaxel versus paclitaxel and carboplatin as second-line therapy in disseminated melanoma: a multicentre trial of the Dermatologic Co-operative Oncology Group (DeCOG)", Melanoma Res., 2003, 13:531-536.
U.S. Appl. No. 14/432,979, office action dated Jan. 7, 2019.
U.S. Appl. No. 15/052,336, office action dated Jan. 22, 2019.
U.S. Appl. No. 15/052,623, office action dated Jan. 7, 2019.
U.S. Appl. No. 15/092,433; office action dated Dec. 12, 2018.
U.S. Appl. No. 15/187,672, office action dated Nov. 28, 2018.
U.S. Appl. No. 15/331,754; office action dated Feb. 22, 2019.
U.S. Appl. No. 15/412,536; office action dated Oct. 1, 2018.
U.S. Appl. No. 15/412,581; office action dated Nov. 13, 2018.
U.S. Appl. No. 15/412,596, office action dated Dec. 27, 2018.
U.S. Appl. No. 15/414,526; office action dated Nov. 16, 2018.
U.S. Appl. No. 15/414,533; office action dated Nov. 19, 2018.
U.S. Appl. No. 15/452,669, office action dated Nov. 26, 2018.
Elst et al. "Epidermal Growth Factor Receptor Expression and Activity In Acute Myeloid Leukemia", Blood 116:3144 (2010), abstract.
Lin, "Salmon Calcitonin: Conformational Changes and Stabilizer Effects", AIMS Biophysics, 2015, 2(4): 695-723.

(56) References Cited

OTHER PUBLICATIONS

Lloyd et al. "Modelling the human immune response: performance of a 1011 human antibody repertoire against a broad panel of therapeutically relevant antigens", Protein Eng. , Design & Selection 22(3):159-168 (2009).
International Preliminary Report on Patentability for Application No. PCT/US2017/050134, dated Mar. 21, 2019.
Anonymous, "Phase I/II Study of Abraxane in Recurrent and Refractory Lymphoma", NCT01555853, ClinicalTrials.gov, Jun. 6, 2014 (8 pages).
U.S. Appl. No. 15/092,403, office action dated May 23, 2019.
U.S. Appl. No. 15/092,433, office action dated May 30, 2019.
U.S. Appl. No. 15/225,428, office action dated Jul. 31, 2019.
U.S. Appl. No. 15/225,542; office action dated Jul. 18, 2019.
U.S. Appl. No. 15/286,024, office action dated Aug. 1, 2019.
U.S. Appl. No. 15/359,569, office action dated Jul. 26, 2019.
U.S. Appl. No. 15/412,581; office action dated Mar. 8, 2019.
U.S. Appl. No. 15/412,610, office action dated Mar. 14, 2019.
U.S. Appl. No. 15/414,526; office action dated Mar. 12, 2019.
U.S. Appl. No. 15/414,533; office action dated Mar. 8, 2019.
U.S. Appl. No. 15/430,411, office action dated May 1, 2019.
U.S. Appl. No. 15/452,669; office action dated Jun. 24, 2019.
U.S. Appl. No. 15/456,377; office action dated Mar. 19, 2019.
U.S. Appl. No. 15/456,377; office action dated Jul. 5, 2019.
U.S. Appl. No. 15/456,382; office action dated Mar. 18, 2019.
U.S. Appl. No. 15/456,382; office action dated Jul. 8, 2019.
U.S. Appl. No. 15/456,391; office action dated Mar. 15, 2019.
U.S. Appl. No. 15/456,391; office action dated Jul. 24, 2019.
U.S. Appl. No. 15/456,395; office action dated Mar. 28, 2019.
U.S. Appl. No. 15/456,395; office action dated Aug. 14, 2019.
U.S. Appl. No. 15/456,399; office action dated Mar. 28, 2019.
U.S. Appl. No. 15/456,399; office action dated Aug. 14, 2019.
U.S. Appl. No. 15/460,552; office action dated Apr. 1, 2019.
U.S. Appl. No. 15/460,552; office action dated Aug. 14, 2019.
U.S. Appl. No. 15/460,699; office action dated Mar. 28, 2019.
U.S. Appl. No. 15/461,288; office action dated Apr. 1, 2019.
Bedu-Addo "Understanding Lyophilization Formulation Development", Pharmaceutical Technology Lyophilization. pp. 10-18 (2004).
Beers et al. "CD20 as a Target for Therapeutic Type I and II Monoclonal Antibodies", Seminars in Hematology 47(2):107-114 (2010).
Belidegrun et al. "Human Renal Carcinoma Line Transfected with Interleukin-2 and/or Interferon alpha Gene(s): Implications for Live Cancer Vaccines", J National Cancer Institute 85(3):207-216 (1993).
Buechner "Intralesional interferon alfa-2b in the treatment of basal cell carcinoma", J Am Acad Dermatol 24:731-734 (1991).
Cheng et al. Molecularly targeted drugs for metastatic colorectal cancer. Drug Des Devel Ther. Nov. 1, 2013 ;7:1315-22 (Year: 2013).
Coiffier "The Role of Rituximab in Lymphomas", Rev. Bras. Hematol. Hemoter., 2002, vol. 24, No. 3, ISSN: 1516-8484 (6 pages).
Dovell et al. "Adjuvant Therapy of Stage IIIb Melanoma with Interferon Alfa-2b:Clinical and Immunological Relevance", Dermatology 191:234-239 (1995).
Edwards et al. The Remarkable Flexibility of the Human Antibody Repertoire; Isolation of Over One Thousand Different Antibodies to a Single Protein, BLyS', J. Mol. Biol 334:103-118 (2003).
European Application No. 16837869.3, Extended European Search Report dated Apr. 4, 2019.
European Application No. 17736453.6, Extended European Search Report dated Jul. 8, 2019.
International Preliminary Report on Patentability for Application No. PCT/US2017/045643, dated Feb. 14, 2019.
International Preliminary Report on Patentability for Application No. PCT/US2017/049745, dated Mar. 14, 2019.
International Preliminary Report on Patentability for Application No. PCT/US2017/049746, dated Mar. 14, 2019.
International Preliminary Report on Patentability for Application No. PCT/US2017/050137, dated Mar. 21, 2019.
Iqbal et al. Anti-Cancer Actions of Denosumab. Curr Osteoporos Rep. Dec. 2011;9(4): 173-6, (Year: 2011).
Khallout et al. "5-Fluorouracil and interferon-alpha Immunochemotherapy enhances Immunogenicity of Murine Pancreatic Cancer Through Upregulation of NKG2D Ligands and MHC Class 1", Immunother 35(3):245-253 (2012).
Korthals et al. "Monocyte derived dendritic cells generated by IFN-alpha acquire mature dendritic and natural killer cell properties as shown by gene expression analysis", J Translated Medicine 5:46 (2007) (11 pages).
Krishnan et al., "Programmed death-1 receptor and interleukin-10 in liver transplant recipients at high risk for late cytomegalovirus disease", Transpl Infect Dis., 12(4):363-70, print Aug. 2010, ePub Jan. 2010.
Matthey et al, Promising therapeutic targets in neuroblastoma. Clin Cancer Res. May 15, 2012; 18(10):2740-53. (Year: 2012).
Package Insert, Caropaih® (Alemtuzumab), Millennium and ILEX Partners, LP, 13 pages, available May 2001.
Reck et al. "Ipilimumab in combination with paclitaxel and carboplatin as first-line therapy in extensive-disease-small-cell lung cancer results from a randomized, double-blind, multicenter phase 2 trial", Ann Oncol. 24(1):75-83 (2013).
Robak, T. Emerging monoclonal antibodies and related agents for the treatment of chronic lymphocytic leukemia. Future Oneal. Jan. 2013;9(1):69-91, Abstract Only. (Year: 2013).
Verma et al. "Effect of surface properties on nanoparticle-cell interactions", Small. 6(1 ): 12-21. (2010).
U.S. Appl. No. 15/225,428, office action dated Dec. 6, 2019.
U.S. Appl. No. 15/225,542, office action dated Jan. 14, 2020.
U.S. Appl. No. 15/286,024, office action dated Feb. 10, 2020.
U.S. Appl. No. 15/359,569; office action dated Jan. 17, 2020.
U.S. Appl. No. 15/430,411, office action dated Apr. 17, 2020.
U.S. Appl. No. 15/452,669; office action dated Mar. 3, 2020.
U.S. Appl. No. 15/456,377; office action dated Mar. 12, 2020.
U.S. Appl. No. 15/456,391; office action dated Feb. 4, 2020.
U.S. Appl. No. 15/460,699; office action dated Mar. 3, 2020.
U.S. Appl. No. 15/461,288; office action dated Feb. 28, 2020.
U.S. Appl. No. 15/752,155; office action dated Feb. 7, 2020.
U.S. Appl. No. 16/328,146; office action dated Feb. 26, 2020.
Barua et al. "Particle shape enhances specificity of antibody-display nanoparticles", PNAS 110(9):3270-3275 (2013).
Chuang et al. "Recombinant human serum albumin", Drugs Today 43(8):547-561 (2007) (Abstact Only) (2 pages).
European Application No. 17750912.2 Extended European Search Report dated Jan. 2, 2020.
Miele et al. "Albumin-bound formulation of paclitaxel (Abraxane® ABI-007) in the treatment of breast cancer", International Journal of Nanomedicine 4:99-105 (2009).
Warner et al. "Alemtuzumab use in relapsed and refractory chronic lymphocytic leukemia: a history and discussion of future rational use", Ther Adv Hematol 3(6):375-389 (2012).
Zhao et al. "Abraxane, the Nanoparticle Formulation of Paclitaxel Can Induce Drug Resistance by Ip-Regulation of P-gp", PLoS One 10(7):e0131429 (2015) (19 pages).
U.S. Appl. No. 15/430,411; office action dated Oct. 31, 2019.
Anonymous "Paclitaxel Abumin-Stabilized Nanoparticie Formulation and Bevacizumab in Treating Patients With Stage IV Melanoma That Cannot Be Removed by Surgery or Gynecological Cancers", NCT02020707, Clinica/Trials.gov, Dec. 25, 2013 (13 pages).
U.S. Appl. No. 15/675,596; office action dated Dec. 3, 2019.
Reynolds at al. "Phase II Trial of Nanoparticle Albumin-Bound Paclitaxel, Carboplatin, and Bevacizumab in First-Line Patients with Advanced Nonsquamaus Non-small Cell Lung Cancer", J Thoracic Oncology 4(12):1537-1549 (2009).
U.S. Appl. No. 15/225,542; office action dated Jul. 30, 2020.
U.S. Appl. No. 15/286,024, office action dated Jul. 29, 2020.
U.S. Appl. No. 15/359,569; office action dated Aug. 10, 2020.
U.S. Appl. No. 15/675,596; office action dated May 28, 2020.
U.S. Appl. No. 16/328,146; office action dated Jul. 28, 2020.
Abraxis Bioscience, Inc., "Abrexane: For the adjuvant treatment of node-positive breast cancer administered sequentially to standard doxorubicin-containing combination chemotherapy," Oncologic Drugs Advisory Committee Meeting (available to public Aug. 4, 2006).

(56) References Cited

OTHER PUBLICATIONS

Notification of Transmittal of the Internatianal Search Report and the Written Opinion of the International Searching Authority, or the Declaration corresponding to International Application No. PCT/US2017/023442 dated Jun. 16, 2017.
Notification of Transmittal of the International Search Report and the Written Opinion of the International Searching Authority, or the Declaration corresponding to International Application No. PCT/US2017/023443 dated Jul. 11, 2017.
Vishnu et al., "Safety and Efficacy of nab-Paclitaxel in the Treatment of Patients with Breast cancer," Breast Cancer: Basic and Clinical Research. 2011, vol. 5, pp. 53-65.
International Preliminary Report on Patentability for Application No. PCT/US2017/023442, dated Oct. 4, 2018.
International Preliminary Report on Patentability for Application No. PCT/US2017/023443, dated Oct. 4, 2018.
"U.S. Appl. No. 15/430,411, office action dated Nov. 2, 2020".
"U.S. Appl. No. 15/452,669; office action dated Oct. 21, 2020".
"U.S. Appl. No. 15/456,377; office action dated Sep. 1, 2020".
"U.S. Appl. No. 15/675,596; office action dated Oct. 20, 2020".
"U.S. Appl. No. 16/086,977; office action dated Sep. 3, 2020".
"U.S. Appl. No. 16/330,028; office action dated Nov. 24, 2020".

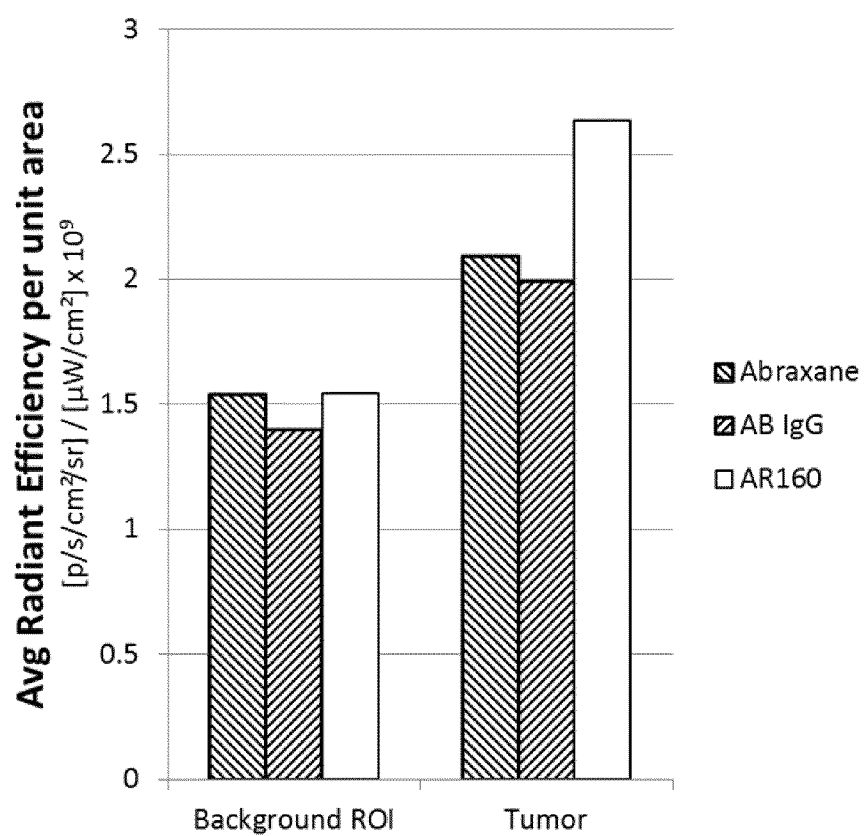

METHODS FOR REDUCING TOXICITY OF A CHEMOTHERAPEUTIC DRUG

CROSS REFERENCE TO RELATED APPLICATIONS

This application is a 35 U.S.C. § 371 national phase application of PCT Application PCT/US2017/023443 filed Mar. 21, 2017, which claims priority under 35 § 119(e) to U.S. Provisional Application No. 62/311,327, filed Mar. 21, 2016, the entire contents each of which are incorporated herein by reference in its entirety.

BACKGROUND

Chemotherapy remains a mainstay for systemic therapy for many types of cancer, including pancreatic cancer and melanoma. Most chemotherapeutic drugs are only slightly selective to tumor cells, and toxicity to healthy proliferating cells can be high (Allen™. (2002) Cancer 2:750-763), often requiring dose reduction and even discontinuation of treatment. In theory, one way to overcome chemotherapy toxicity issues as well as improve drug efficacy is to target the chemotherapy drug to the tumor using antibodies that are specific for proteins selectively expressed (or overexpressed) by tumors cells to attract targeted drugs to the tumor. The desired result is altered bio-distribution of the chemotherapy, with more drug going to the tumor and less affecting healthy tissue. Despite 30 years of research, however, specific targeting rarely succeeds in the therapeutic context.

Many chemotherapeutic drugs have been approved by regulatory agencies (e.g., the Food and Drug Administration, FDA) for treatment of various types of cancer. However, many more chemotherapeutic drugs have been rejected, despite efficacy, because the drug is toxic to one or more tissues in the patient, and such toxicity outweighs any benefit.

This disclosure provides methods for reducing toxicity of chemotherapeutic agents to improve the therapeutic index.

SUMMARY OF THE INVENTION

The risks of irreversible toxicities, such as direct chemotherapy-induced hepatotoxicity or potentiation of preexisting liver disease, continue to exist for many currently available therapeutics. It is common for potential chemotherapeutic drugs to be abandoned by drug companies or rejected by regulatory agencies because the toxicity to non-target tissues exceeds the therapeutic benefit. There remains a need for anti-cancer therapeutics with decreased toxicities that can efficiently target tumor cells in order to treat cancer in a patient. Embodiments herein generally relate to compositions and methods that result in improved safety for cancer therapies that otherwise have unacceptably high toxicity in patients.

The instant technology generally relates to methods for decreasing toxicity, thereby increasing the therapeutic index, of a chemotherapeutic drug by combining the drug with a protein carrier and an antibody or other molecule (e.g., aptamer) that targets the resulting complex to an aberrant cell (e.g., tumor cell). It is contemplated that the methods as described herein will also increase efficacy of the drug, further increasing the therapeutic index. In some embodiments, the toxicity of the drug is decreased, at least in part, by an increase in uptake of the drug by the aberrant cells.

In particular, the present disclosure relates to compositions for decreasing toxicity of and/or providing an acceptable therapeutic index for a chemotherapy drug, using antibody therapy with nanoparticles comprising a protein core, such as albumin, or other biocompatible and preferably human carrier protein and, associated with the surface of that core, antibodies, aptamers, or other proteins (e.g. fusion protein) having a region that associates with the carrier protein/protein core while retaining the binding function of the antibody, aptamer or other binding agents (e.g., protein) to the target ligand on the surface of the particle (e.g., the binding region of the antibody, aptamer or other binding agent is exposed outside of the particle or is available notwithstanding the interaction of the carrier protein binding portion).

Without being limited to any theory, it is believed that this invention increases the therapeutic index by rendering the drug less toxic. The lower toxicity allows more drug to be delivered while maintaining acceptable side effects. It is also contemplated that the drug is more efficacious, and as such less drug can be used to get the same results provided by previous compositions. This combination allows for an increase in the therapeutic index by raising the ceiling and lowering the floor, and results in an acceptable therapeutic index for chemotherapy agents that otherwise are unacceptable for treating humans. Such a combination is surprising and typically not known.

An acceptable therapeutic index is one which indicates a therapeutic effect that outweighs toxicity. In some embodiments, an acceptable therapeutic index is one which would lead to continued pursuit of the chemotherapeutic drug, e.g., clinical trials and/or regulatory agency approval.

In one aspect is provided a method for providing an acceptable therapeutic index of a chemotherapeutic drug targeting aberrant mammalian cells, which method comprises:
 a) combining a therapeutically effective amount of the drug with a biocompatible protein carrier, wherein the drug has an unacceptable therapeutic index when administered alone;
 b) forming a complex with the carrier and an effective amount of an antibody or aptamer which has specificity to an antigen on the aberrant cells, wherein the antibodies or aptamers populate the surface of the complex and retain binding specificity; and
 c) administering the complex to a patient, wherein administration enhances delivery of the drug to the cells and reduces one or more side effects of the drug, thereby increasing the therapeutic index of the drug to provide an acceptable therapeutic index.

In one aspect is provided a method for providing an acceptable therapeutic index of a chemotherapeutic drug targeting tumor cells, which method comprises:
 a) combining a therapeutically effective amount of the drug with an albumin carrier, wherein the drug has an unacceptable therapeutic index when administered alone;
 b) forming a complex with the carrier and an effective amount of antibody or aptamer which has specificity to an antigen on the tumor cells, wherein the antibodies or aptamers populate the surface of the complex and retain binding specificity; and
 c) administering the complex to a patient wherein administration enhances delivery of the drug to the tumor cells and reduces one or more side effects of the drug, thereby increasing the therapeutic index of the drug.

In one embodiment, the complex is less than 1 micron in diameter. In one embodiment, the complex has a diameter of between 0.1 and 0.9 microns.

In one aspect, this disclosure relates to a method of reducing chemotherapy drug-related toxicity in a patient having cancer, which method comprises treating the patient with a complex comprising a therapeutically effective amount of a chemotherapy drug with an albumin carrier, and an effective amount of antibody or aptamer which has specificity to an antigen on the cancer, wherein the antibodies populate the surface of the complex and retain binding specificity, wherein the chemotherapy drug has an unacceptable therapeutic index when administered alone, such that the patient has reduced risk of chemotherapy drug-related toxicity.

In one aspect, this disclosure relates to a method for providing an acceptable therapeutic index of a chemotherapeutic drug targeting aberrant mammalian cells, which method comprises:
  a) combining a therapeutically effective amount of the drug with a biocompatible protein carrier, wherein the drug has an unacceptable therapeutic index when administered alone;
  b) forming a complex with the carrier and an effective amount of binding agent having specificity to the aberrant cells, wherein the binding agent populates the surface of the complex and retains specificity, and further wherein the binding agent has a protein carrier-binding portion; and
  c) administering the complex to a patient, wherein administration enhances delivery of the drug to the cells and reduces one or more side effects of the drug, thereby increasing the therapeutic index of the drug.

In one embodiment, the binding agents are aptamers, antibodies, fusion proteins, or Fc receptors. Preferably, the binding agent includes a carrier protein-binding portion (e.g., albumin-binding portion), e.g. at an end opposite the binding moiety. It is contemplated that surface complexation of the antibody occurs through the carrier protein-binding portion of the binding agent, which results in all or part of the carrier protein-binding portion being associated with the protein core, while the binding portions (regions) (e.g., Fa and Fb portions, nucleic acid, etc.) of the binding agent remain outside of the protein core, thereby retaining their target-specific binding capabilities. In a preferred embodiment, the binding agents are antibodies.

In one embodiment, the aberrant mammalian cells are cancer cells, cells involved in an auto-immune disease, cells involved in an inflammatory disease, virus-infected cells, or bacteria-infected cells.

In one embodiment, the protein carrier is albumin, gelatin, elastin, gliadin, legumin, zein, soy protein, milk protein, or whey protein. Preferably, the protein carrier is albumin.

In one embodiment, the complex comprises an effective amount of paclitaxel to provide stability to the complex. In one embodiment, the amount of paclitaxel is less than the therapeutically effective amount of paclitaxel.

In one embodiment, drug-related toxicity is reduced. In one embodiment, the chemotherapy drug-related toxicity is cardiotoxicity, nephrotoxicity, hepatotoxicity, pulmonary toxicity, dermatologic toxicity, or gastrointestinal toxicity.

BRIEF DESCRIPTION OF THE DRAWINGS

FIG. 1 is a graph indicating the average radiant efficiency per unit area of background or tumors in mice injected with alexaflor 750-labeled ABRAXANE, ABRAXANE coated with non-specific antibody (AB IgG) or ABRAXANE coated with Rituximab (AR160).

DETAILED DESCRIPTION

After reading this description it will become apparent to one skilled in the art how to implement the invention in various alternative embodiments and alternative applications. However, all the various embodiments of the present invention will not be described herein. It will be understood that the embodiments presented here are presented by way of an example only, and not limitation. As such, this detailed description of various alternative embodiments should not be construed to limit the scope or breadth of the present invention as set forth below.

Before the present invention is disclosed and described, it is to be understood that the aspects described below are not limited to specific compositions, methods of preparing such compositions, or uses thereof as such may, of course, vary. It is also to be understood that the terminology used herein is for the purpose of describing particular aspects only and is not intended to be limiting.

The detailed description of the invention is divided into various sections only for the reader's convenience and disclosure found in any section may be combined with that in another section. Titles or subtitles may be used in the specification for the convenience of a reader, which are not intended to influence the scope of the present invention.

Definitions

Unless defined otherwise, all technical and scientific terms used herein have the same meaning as commonly understood by one of ordinary skill in the art to which this invention belongs. In this specification and in the claims that follow, reference will be made to a number of terms that shall be defined to have the following meanings:

The terminology used herein is for the purpose of describing particular embodiments only and is not intended to be limiting of the invention. As used herein, the singular forms "a", "an" and "the" are intended to include the plural forms as well, unless the context clearly indicates otherwise.

"Optional" or "optionally" means that the subsequently described event or circumstance can or cannot occur, and that the description includes instances where the event or circumstance occurs and instances where it does not.

The term "about" when used before a numerical designation, e.g., temperature, time, amount, concentration, and such other, including a range, indicates approximations which may vary by (+) or (−) 10%, 5%, 1%, or any subrange or subvalue there between. Preferably, the term "about" when used with regard to a dose amount means that the dose may vary by +/−10%.

"Comprising" or "comprises" is intended to mean that the compositions and methods include the recited elements, but not excluding others. "Consisting essentially of" when used to define compositions and methods, shall mean excluding other elements of any essential significance to the combination for the stated purpose. Thus, a composition consisting essentially of the elements as defined herein would not exclude other materials or steps that do not materially affect the basic and novel characteristic(s) of the claimed invention. "Consisting of" shall mean excluding more than trace elements of other ingredients and substantial method steps. Embodiments defined by each of these transition terms are within the scope of this invention.

The term "antibody" or "antibodies" as used herein refers to immunoglobulin molecules and immunologically active portions of immunoglobulin molecules (i.e., molecules that contain an antigen binding site that immuno-specifically bind an antigen). The term also refers to antibodies comprised of two immunoglobulin heavy chains and two immunoglobulin light chains as well as a variety of forms including full length antibodies and portions thereof; including, for example, an immunoglobulin molecule, a monoclonal antibody, a chimeric antibody, a CDR-grafted antibody, a humanized antibody, a Fab, a Fab', a F(ab')2, a Fv, a disulfide linked Fv, a scFv, a single domain antibody (dAb), a diabody, a multispecific antibody, a dual specific antibody, an anti-idiotypic antibody, a bispecific antibody, a functionally active epitope-binding fragment thereof, bifunctional hybrid antibodies (e.g., Lanzavecchia et al., *Eur. J. Immunol.* 17, 105 (1987)) and single chains (e.g., Huston et al., *Proc. Natl. Acad. Sci. U.S.A.*, 85, 5879-5883 (1988) and Bird et al., *Science* 242, 423-426 (1988), which are incorporated herein by reference). (See, generally, Hood et al., *Immunology*, Benjamin, N.Y., 2ND ed. (1984); Harlow and Lane, *Antibodies. A Laboratory Manual*, Cold Spring Harbor Laboratory (1988); Hunkapiller and Hood, *Nature,* 323, 15-16 (1986), which are incorporated herein by reference). The antibody may be of any type (e.g., IgG, IgA, IgM, IgE or IgD). Preferably, the antibody is IgG. More preferably, the antibody contains a Fc domain. An antibody may be non-human (e.g., from mouse, goat, or any other animal), fully human, humanized, or chimeric. Where a particular antibody (e.g., bevacizumab) is recited herein as the antibody, it is contemplated that a different antibody can be substituted.

The term "antigen" is well understood in the art and includes substances which are immunogenic. As used herein, the term "antigen" may also refer to a substance to which a binding agent other than an antibody (e.g., an aptamer) can bind.

The term "aptamer" as used herein relates to a single-stranded DNA or RNA molecule or peptide that binds to a target, for example, small molecules, toxins, peptides, proteins, viruses, bacteria, and even whole cells. Aptamers can be engineered and then selected from large random sequence pools. To increase stability and binding affinity, nucleic acid aptamers may include unnatural or modified bases and/or a mini hairpin structure.

The term "binding agent" is generic to antibodies, aptamers modified to contain a protein carrier-binding region, fusion proteins, and the like.

The term "biosimilar" as used herein refers to a biopharmaceutical which is deemed to be comparable in quality, safety, and efficacy to a reference product marketed by an innovator company.

The term "carrier protein" or "protein carrier" as used herein refers to proteins that function to transport therapeutic agents, antibodies, or both. Examples of carrier proteins are discussed in more detail below. Where albumin is recited herein as the carrier protein, it is contemplated that a different carrier protein can be substituted.

The term "dose" and "dosage" refer to an amount of binding agent (e.g., antibody or aptamer) or chemotherapeutic drug given to a patient in need thereof. The attending clinician will select an appropriate dose from the range based on the patient's weight, age, health, stage of cancer, level of circulating antigen, and other relevant factors, all of which are well within the skill of the art. The term "unit dose" refers to a dose of the binding agent or chemotherapeutic drug that is given to the patient to provide a desired result. In some instances, the unit dose is sold in a subtherapeutic formulation (e.g., 10% of the therapeutic dose). The unit dose may be administered as a single dose or a series of subdoses. Additionally, some terms used in this specification are more specifically defined below.

An "effective amount" intends to indicate the amount of a compound or agent (e.g., a chemotherapeutic drug) administered or delivered to the patient which is most likely to result in the desired treatment outcome. The amount is empirically determined by the patient's clinical parameters including, but not limited to the stage of disease, age, gender, histology, and likelihood for recurrence. In addition, the level of circulating antigen can be used to empirically determine the effective amount of the chemotherapeutic drug and/or binding agent to administer to a patient.

The term "express" as applied to an antigen, refers to the amount of the antigen produced by a cancer. In one aspect, the amount is determined by measuring the expression level of an antigen of interest (e.g., VEGF) for a given patient population or control population (e.g. population without cancer), determining the median expression level of that antigen for the population, and comparing the expression level of the same antigen for a patient to the median expression level for the given patient population. For example, if the expression level of an antigen of interest for the patient is determined to be above the median expression level of the patient population or the control population, that patient is determined to have high expression of the antigen of interest. "Overexpression" of an antigen in a sample collected from a patient refers to an increase (i.e., high) of the antigen in the sample. For example, overexpression can be about 1.5 times, or alternatively, about 2.0 times, or alternatively, about 2.5 times, or alternatively, about 3.0 times, or alternatively, about 5 times, or alternatively, about 10 times, or alternatively about 50 times, or yet further alternatively more than about 100 times higher than the expression level detected in a control sample collected from a person not having cancer. Alternatively, if the expression level of an antigen of interest for the patient is determined to be below the median expression level of the patient population, that patient is determined to have low expression of the antigen of interest.

The term "hepatic impairment" refers to any liver damage that reduces liver function. Diseases (e.g. hepatitis) or traumatic injury (e.g., chemical, drugs, alcohol) are non-limiting examples that may reduce normal liver activities.

The terms "lyophilized," "lyophilization" and the like as used herein refer to a process by which the material (e.g., nanoparticles) to be dried is first frozen and then the ice or frozen solvent is removed by sublimation in a vacuum environment. An excipient may be included in pre-lyophilized formulations to enhance stability of the lyophilized product upon storage. In some embodiments, the carrier protein, therapeutic agent, binding agent, or any combination thereof is lyophilized separately. In other embodiments, the carrier protein, therapeutic agent, binding agent, or any combination thereof is first combined and then lyophilized. The lyophilized sample may further contain additional excipients.

The term "nanoparticle" as used herein refers to particles with at least one dimension less than 5 microns. In some embodiments, the nanoparticle is less than 1 micron. For direct administration, the nanoparticle may be larger. Even larger particles are expressly contemplated by the invention. The terms "conjugate" and "complex" as used herein are synonymous with "nanoparticle." The term "nanoparticle" may also encompass discrete multimers of smaller unit nanoparticles. For example, a 320 nm particle comprises a dimer of a unit 160 nm nanoparticle. For 160 nm nanoparticles, multimers would therefore be approximately 320 nm, 480 nm, 640 nm, 800 nm, 960 nm, 1120 nm, and so on as determined by a Mastersizer 2000 (available from Malvern Instruments Ltd, Wocestershire, UK) as described in PCT/US15/54295.

In a population of particles, the size of individual particles is distributed about a mean. Particle sizes for the population can therefore be represented by an average, and also by percentiles. D50 is the particle size below which 50% of the particles fall. 10% of particles are smaller than the D10 value and 90% of particles are smaller than D90. Where unclear, the "average" size is equivalent to D50.

As used herein, the term "therapeutic index" with regard to a chemotherapeutic drug (agent) indicates safety of the chemotherapeutic drug. In some aspects, the therapeutic index can include a comparison of the amount of a therapeutic agent that causes the therapeutic effect (e.g., killing cancer cells) to the amount of the therapeutic agent that causes toxicity (e.g., liver toxicity). The larger the therapeutic index, the safer the drug is. It is contemplated that according to certain embodiments an improved therapeutic index can occur using the compositions and/or methods described herein, including without limitation when: (1) the dosage of chemotherapeutic agent is increased above the current therapeutic dosages; (2) the dosage of chemotherapeutic agent remains the same as the current therapeutic dosages; or (3) the dosage of chemotherapeutic agent is decreased below the current therapeutic dosages. In some embodiments, the compositions and methods, including the specifically numbered scenarios in this paragraph can elicit improved or similar therapeutic effect as seen with the current therapeutic dosages with no worse, fewer, or no toxicities.

As used herein, the phrase "unacceptable therapeutic index" refers to a therapeutic index that is too low for the drug to be pursued as a chemotherapeutic drug. That is, the toxicity of the drug to a patient outweighs any therapeutic effect, such that a drug company or clinical researcher would not pursue the drug as a potential therapeutic drug (e.g., would not have additional clinical or pre-clinical trials with the drug), and/or a regulatory agency (e.g., the FDA) would not approve the drug for use.

As used herein, the term "therapeutic effect" refers to achievement of the desired and/or beneficial consequences of a medical treatment. A non-limiting example of a therapeutic effect of the present disclosure is the shrinkage and/or eradication of a tumor and/or killing of cancer cells in a patient.

The term "treating" or "treatment" covers the treatment of a disease or disorder (e.g., cancer), in a subject, such as a human, and includes: (i) inhibiting a disease or disorder, i.e., arresting its development; (ii) relieving a disease or disorder, i.e., causing regression of the disorder; (iii) slowing progression of the disorder; and/or (iv) inhibiting, relieving, or slowing progression of one or more symptoms of the disease or disorder. In some embodiments "treating" or "treatment" refers to the killing of cancer cells. In some embodiments "treating" or "treatment" refers to increasing progression-free survival of the patient(s). In some embodiments "treating" or "treatment" refers to increasing survival rates.

An effective amount or a therapeutically effective amount or dose of an agent, e.g., a compound of the invention, refers to that amount of the agent or compound that results in amelioration of symptoms or a prolongation of survival in a subject. Toxicity and therapeutic efficacy of such molecules can be determined by standard pharmaceutical procedures in cell cultures or experimental animals, e.g., by determining the LD50 (the dose lethal to 50% of the population) and the ED50 (the dose therapeutically effective in 50% of the population). The dose ratio of toxic to therapeutic effects is the therapeutic index, which can be expressed as the ratio LD50/ED50. Agents that exhibit high therapeutic indices are preferred.

A "therapeutically effective amount of paclitaxel" is an amount of paclitaxel which is generally used to treat cancer in a patient. For example, the recommended dose for adults, depending on the cancer to be treated, is 50 milligrams per square meter of patient surface area ($mg/m^2$) to 175 $mg/m^2$. See. e.g., www.drugs.com/dosage/paclitaxel.html. Thus, "less than a therapeutically effective amount" or "sub-therapeutic amount" of paclitaxel refers to an amount of paclitaxel that is less than the therapeutic amount, e.g., 0.1 $mg/m^2$ to 100 $mg/m^2$, or 0.1 $mg/m^2$ to 50 $mg/m^2$, or 1 $mg/m^2$ to 50 $mg/m^2$, or 1 $mg/m^2$ to 40 $mg/m^2$. The amount may be or any subrange or value between any ranges provided.

A "stable" formulation is one in which the protein therein essentially retains its physical stability and/or chemical stability and/or biological activity upon storage. For example, various analytical techniques for measuring protein stability are available in the art and are reviewed in Peptide and Protein Drug Delivery, 247-301, Vincent Lee Ed., Marcel Dekker, Inc., New York, N.Y., Pubs. (1991) and Jones, A. Adv. Drug Delivery Rev. 10:29-90 (1993). Stability can be measured at a selected temperature for a selected time period.

Methods

As will be apparent to the skilled artisan upon reading this disclosure, the present disclosure relates to methods for reducing toxicity, thereby improving the therapeutic index of a chemotherapeutic drug in the treatment of a patient having aberrant cells. In a preferred embodiment, the patient is afflicted with cancer.

The risks of irreversible toxicities, such as direct chemotherapy-induced hepatotoxicity or potentiation of preexisting liver disease, continue to exist for many currently available therapeutics. It is common for potential chemotherapeutic drugs to be abandoned by drug companies or rejected by regulatory agencies because the toxicity to non-target tissues exceeds the therapeutic benefit. There remains a need for anti-cancer therapeutics with decreased toxicities that can efficiently target tumor cells in order to treat cancer in a patient. Embodiments herein generally relate to compositions and methods that result in improved safety for cancer therapies that otherwise have an unacceptable therapeutic index.

In particular, the present disclosure relates to methods for increasing the therapeutic index of a chemotherapeutic drug (e.g., lowering toxicity, increasing tumor up-take of the drug, increasing efficacy, etc.) by combining the drug with a protein carrier and an antibody or other molecule that targets the resulting complex to an aberrant cell (e.g., tumor cell).

An acceptable therapeutic index is one which indicates a therapeutic effect that outweighs toxicity. In some embodiments, an acceptable therapeutic index is one which would lead to continued pursuit of the chemotherapeutic drug, e.g., clinical trials and/or regulatory agency approval.

In one aspect is provided a method for providing an acceptable therapeutic index of a chemotherapeutic drug targeting aberrant mammalian cells, which method comprises:
  a) combining a therapeutically effective amount of the drug with a biocompatible protein carrier, wherein the drug has an unacceptable therapeutic index when administered alone;

b) forming a complex with the carrier and an effective amount of an antibody or aptamer which has specificity to an antigen on the aberrant cells, wherein the antibodies or aptamers populate the surface of the complex and retain binding specificity; and c) administering the complex to a patient, wherein administration enhances delivery of the drug to the cells and reduces one or more side effects of the drug, thereby increasing the therapeutic index of the drug to provide an acceptable therapeutic index.

In one aspect is provided a method for providing an acceptable therapeutic index of a chemotherapeutic drug targeting tumor cells, which method comprises:

a) combining a therapeutically effective amount of the drug with an albumin carrier, wherein the drug has an unacceptable therapeutic index when administered alone;

b) forming a complex with the carrier and an effective amount of antibody or aptamer which has specificity to an antigen on the tumor cells, wherein the antibodies or aptamers populate the surface of the complex and retain binding specificity; and c) administering the complex to a patient wherein administration enhances delivery of the drug to the tumor cells and reduces one or more side effects of the drug, thereby increasing the therapeutic index of the drug.

In one embodiment, the complex is less than 1 micron in diameter.

In one aspect, this disclosure relates to a method of reducing chemotherapy drug-related toxicity in a patient having cancer, which method comprises treating the patient with a complex comprising a therapeutically effective amount of a chemotherapy drug with an albumin carrier, and an effective amount of antibody or aptamer which has specificity to an antigen on the cancer, wherein the antibodies populate the surface of the complex and retain binding specificity, wherein the chemotherapy drug has an unacceptable therapeutic index when administered alone, such that the patient has reduced risk of chemotherapy drug-related toxicity.

In one aspect, this disclosure relates to a method for providing an acceptable therapeutic index of a chemotherapeutic drug targeting aberrant mammalian cells, which method comprises:

a) combining a therapeutically effective amount of the drug with a biocompatible protein carrier, wherein the drug has an unacceptable therapeutic index when administered alone;

b) forming a complex with the carrier and an effective amount of binding agent having specificity to the aberrant cells, wherein the binding agent populates the surface of the complex and retains specificity, and further wherein the binding agent has a protein carrier-binding portion; and c) administering the complex to a patient, wherein administration enhances delivery of the drug to the cells and reduces one or more side effects of the drug, thereby increasing the therapeutic index of the drug.

In one embodiment, the binding agents are aptamers, antibodies, fusion proteins, or Fc receptors. Preferably, the binding agent includes a protein carrier-binding portion, e.g. at an end opposite the binding moiety. It is contemplated that surface complexation of the antibody occurs through the protein carrier-binding portion (e.g., albumin-binding portion) of the binding agent (such as the Fc component of the antibodies recited herein), while the binding portions (regions) (e.g., Fa and Fb portions, nucleic acid, etc.) of the binding agent remain outside of the protein core, thereby retaining their target-specific binding capabilities.

In one embodiment, the aberrant mammalian cells are cancer cells, cells involved in an auto-immune disease, cells involved in an inflammatory disease, virus-infected cells, or bacteria-infected cells.

In one embodiment, the protein carrier is albumin, gelatin, elastin, gliadin, legumin, zein, soy protein, milk protein, or whey protein. In a preferred embodiment, the protein carrier is albumin. In one embodiment, the albumin is human serum albumin (HSA). In one embodiment, the albumin is recombinant albumin, e.g., recombinant HSA.

In one embodiment, drug-related toxicity is reduced. In one embodiment, the chemotherapy drug-related toxicity is cardiotoxicity, nephrotoxicity, hepatotoxicity, pulmonary toxicity, dermatologic toxicity, or gastrointestinal toxicity.

Therapeutic index is a comparison of the amount of a therapeutic agent that causes the therapeutic effect (e.g., killing cancer cells) to the amount of the therapeutic agent that causes toxicity (e.g., liver toxicity). Toxicities of current formulations of chemotherapeutic drugs are known include increased hepatic impairment. As the liver is the site of metabolism for most chemotherapeutic drugs, many agents are hepatotoxic (directly or indirectly). Administration of such therapeutics to patients with hepatic impairments is known to include increased myelosuppression such that these patients must be monitored closely. In addition, some high-risk patients are recommended to not receive chemotherapeutic drugs at all.

Other known toxicities that may result from chemotherapy treatment include, but are not limited to, cardiotoxicity, nephrotoxicity, pulmonary toxicity, dermatologic toxicity, and gastrointestinal toxicity. For example, some chemotherapeutic drugs may cause direct injury to the heart (either acute or chronic). Chemotherapy drugs produce urinary tract/kidney toxicity. Drugs with pulmonary toxicity can cause severe pulmonary effects. Dermatologic toxicity is also common with chemotherapeutic drugs, and include transient rash, photosensitivity, dermatitis, hyperpigmentation, urticaria, nail changes, alopecia, and radiation recall. Gastrointestinal toxicity, including stomatitis or diarrhea, is also common.

In particular, it is contemplated that chemotherapeutic drugs that have a high level of toxicity will benefit from administration of chemotherapeutic drugs in combination with nanoparticles, as described herein. That is, it is contemplated that administration of the chemotherapeutic drug as a nanoparticle (complex) as described herein will result in decreased toxicity of the drug (e.g., to non-target tissues). It is further contemplated that administration of the chemotherapeutic drug as a nanoparticle will result in increased efficacy of the drug. Thus, the combination of the chemotherapeutic drug with the protein core and a targeting antibody may increase the therapeutic index of the drug by both reducing side effects and improving efficacy of the drug, and may result in a formulation of the chemotherapeutic drug that has an acceptable therapeutic index and can be pursued/approved for use in humans having the target disease.

In some embodiments, the patient is screened for hepatic impairment (or risk thereof) prior to administration of the drug. Determination of patients with hepatic impairment or at risk of hepatic impairment can be determined by any method known to those of skill in the art. Non-limiting examples of ways to determine severity of hepatic impairment include The Child-Pugh classification. This classification system groups patients on the basis of two clinical features (encephalopathy and ascites) and three laboratory based parameters (S-albumin, S-bilirubin, and prothrombin time). Increased albumin is due, at least in part, to decreased synthesis by the hepatocytes in chronic liver disease. Increased levels of bilirubin may be due to cholestasis, hepatocellular failure or extrahepatic causes such as hemolysis. The use of markers like serum albumin, prothrombin time and bilirubin is encouraged and abnormalities in these parameters may be better related to drug elimination capacity than other components of the Child-Pugh classification, e.g. encephalopathy and ascites. Impaired hepatic metabolic capacity can also be tested by administration of a probe drug (e.g., CYP3A4) and observing altered pharmacokinetics of the probe. Exogenous markers that have been used to assess different hepatic drug elimination mechanisms are antipyrine, MEGX (lidocaine metabolite), ICG (indocyanine green) and galactose. These, and other, methods can be used alone or in combination to determine whether a patient suffers or is at risk of hepatic impairment.

Paclitaxel has been associated with hepatotoxicity including elevation of serum aminotransferase in approximately 7-26% of patients, with levels greater than 5 times the upper limit of normal in approximately 2% of those receiving paclitaxel. It has been suggested that liver injury that arises during therapy is due, at least in part, to a direct effect of paclitaxel in inhibiting microtubular function.

It is contemplated in some embodiments that an improved therapeutic index can occur using the compositions and/or methods described herein, for example, when: (1) the dosage of chemotherapeutic drug is increased above the current therapeutic dosages; (2) the dosage of chemotherapeutic drug remains the same as the current therapeutic dosages; or (3) the dosage of chemotherapeutic drug is decreased below the current therapeutic dosages. In some embodiments, the compositions and methods, including the specifically numbered scenarios in this paragraph can elicit improved or similar therapeutic effect as seen with the current therapeutic dosages with no worse, fewer or no toxicities.

In some embodiments, the carrier protein can be albumin, gelatin, elastin (including topoelastin) or elastin-derived polypeptides (e.g., α-elastin and elastin-like polypeptides (ELPs)), gliadin, legumin, zein, soy protein (e.g., soy protein isolate (SPI)), milk protein (e.g., β-lactoglobulin (BLG) and casein), or whey protein (e.g., whey protein concentrates (WPC) and whey protein isolates (WPI)). In preferred embodiments, the carrier protein is albumin. In preferred embodiments, the albumin is egg white (ovalbumin), bovine serum albumin (BSA), or the like. In even more preferred embodiments, the carrier protein is human serum albumin (HSA). In some embodiments, the carrier protein is a generally regarded as safe (GRAS) excipient approved by the United States Food and Drug Administration (FDA).

In some embodiments, the antibody or aptamer targets a non-cell membrane bound antigen, for example, VEGF. A commercially available antibody that targets VEGF is AVASTIN®/bevacizumab and biosimilars thereof. In some embodiments, the antibody or aptamer binds to a tumor related antigen, a non-tumor related antigen, or both. A tumor related antigen is an antigenic substance produced in or by tumor cells. It is within the ability of one of skill in the art to determine what is a tumor related antigen.

Table 1 depicts a list of non-limiting list of antibodies for cancer targets.

TABLE 1

| Antibodies for cancer targets | | |
|---|---|---|
| | Antibodies | |
| | Biologic | Treatment(s)/Target(s) |
| Monoclonal antibodies (MAbs) | Rituximab (RITUXAN ®) | Non-Hodgkin lymphoma |
| | Alemtuzumab (CAMPATH ®) | Chronic lymphocytic leukemia (CLL) |
| | Ipilimumab (YERVOY ®) | Metastatic melanoma |
| | Bevacizumab (AVASTIN ®) | Colon cancer, lung cancer, renal cancer, ovarian cancer, glioblastoma multiforme |
| | Cetuximab (ERBITUX ®) | Colorectal cancer, non-small cell lung cancer, head and neck cancer, cervical cancer, glioblastoma, ovarian epithelia, fallopian tube or primary peritoneal cancer, renal cell cancer |
| | Panitumumab (VECTIBIX ®) | Colorectal cancer |
| | Trastuzumab (HERCEPTIN ®) | Breast cancer, Adenocarcinoma |
| | $^{90}$Y-ibritumomab tiuxetan (ZEVALIN ®) | Non-Hodgkin lymphoma |
| | Ado-trastuzumab emtansine (KADYCLA ®, also called TDM-1) | Breast cancer |
| | Brentuximab vedotin (ADCETRIS ®) | Hodgkin lymphoma, Anaplastic large cell lymphoma |
| | Blinatumomab (BLINCYTO) | Acute lymphocytic leukemia (ALL) |
| | Pembrolizumab (KEYTRUDA ®) | PD-1 (melanoma, non-small cell lung cancer) |
| | Nivolumab (OPDIVO ®) | PD-1 (melanoma, non-small cell lung cancer) |
| | Ofatumumab (ARZERRA ®) | Chronic lymphocytic leukemia (CLL) |
| | Pertuzumab (PERJETA ®) | Breast cancer |

TABLE 1-continued

Antibodies for cancer targets
Antibodies

| Biologic | Treatment(s)/Target(s) |
|---|---|
| Obinutuzumab (GAZYVA ®) | Lymphoma |
| Dinutuximab (UNITUXIN ®) | Neuroblastoma |
| Denosumab (PROLIA ®) | Bone metastases, multiple myeloma, giant cell tumor of bone |

In some embodiments, the antibody is selected from the group consisting of ado-trastuzumab emtansine, alemtuzumab, bevacizumab, blinatumomab, brentuximab vedotin, cetuximab, denosumab, dinutuximab, ibritumomab tiuxetan, ipilimumab, nivolumab, obinutuzumab, ofatumumab, panitumumab, pembrolizumab, pertuzumab, rituximab, trastuzumab, or any biosimilar thereof.

In one embodiment, the antibody or other binding agent comprises a protein carrier-binding domain. The protein carrier-binding domain may be any region, domain, amino acid sequence, etc. which allows for interaction (e.g., hydrophobic interaction) between the protein carrier (e.g., albumin) and the binding agent (or portion thereof). In one embodiment, the binding agent is covalently bound to the albumin or other carrier protein. In one embodiment, the binding agent is bound to the albumin or other carrier protein via hydrophobic interactions.

In some aspects, the complexes and compositions as described herein target non-cancer diseases. Non-cancer diseases include, without limitation, inflammatory diseases, autoimmune diseases, and infectious diseases. In one embodiment, the antibody or other binding agent is specific for an epitope associated with an infectious disease. In one embodiment, the disease is caused by a pathogen selected from the group consisting of bacteria, fungus, virus, or parasite infection. In one embodiment, the antibody or other binding agent is specific for an epitope associated with the pathogen. In one embodiment, the antibody or other binding agent is specific for an epitope associated with a toxin produced by the pathogen. In one embodiment, the antibody or other binding agent targets one or more symptoms of the infectious disease.

Tables 2 and 3 depict non-limiting lists of antibodies and fusion proteins for infectious disease targets.

TABLE 2

Antibodies and Fusion Protein for Infectious
Disease (approved or in trials)
Antibodies

| Biologic | Type | Treatment(s) | Target(s) |
|---|---|---|---|
| Palivizumab | Humanized antibody | Respiratory syncytial virus | RSV F protein |
| Actoxumab | Human antibody | *Clostridium difficile* colitis | Exotoxin TcdA |
| Bezlotoxumab | Human antibody | *Clostridium difficile* infection | Exotoxin TcdB |
| N/A | Fusion protein: Toll-like receptor 4 with IgG1 Fc | Bacterial sepsis | |

TABLE 3

Other antibodies for infectious disease uses
Antibodies

| Antibody | Type | Proposed Treatment/Target |
|---|---|---|
| Bezlotoxumab | human | *Clostridium difficile* colitis |
| CR6261 | human | infectious disease, influenza A |
| Diridavumab | human | influenza A |
| Edobacomab | mouse | sepsis caused by Gram-negative bacteria |
| Efungumab | human | invasive *Candida* infection |
| Exbivirumab | human | hepatitis B |
| Felvizumab | humanized | respiratory syncytial virus infection |
| Firivumab | human | influenza |
| Foravirumab | human | rabies |
| Ibalizumab | humanized | HIV infection |
| Libivirumab | human | hepatitis B |
| Motavizumab | humanized | respiratory syncytial virus |
| Obiltoxaximab | chimeric | *Bacillus anthracis* spores |
| Pagibaximab | chimeric | sepsis (*Staphylococcus*) |
| Panobacumab | human | *Pseudomonas aeruginosa* infection |
| Pritoxaximab | chimeric | Anti-Shiga toxin 1 B subunit |
| PRO 140 | humanized | HIV infection |
| VRC01LS | humanized | HIV |
| Rafivirumab | human | rabies |
| Raxibacumab | human | anthrax (prophylaxis and treatment) |
| Regavirumab | human | cytomegalovirus infection |
| Setoxaximab | chimeric | *E. coli* |
| Sevirumab | human | cytomegalovirus infection |
| Suvizumab | humanized | viral infections |
| Tefibazumab | humanized | *Staphylococcus aureus* infection |
| Tosatoxumab | human | Anti-*S. aureus* alpha-toxin |
| Tuvirumab | human | chronic hepatitis B |
| Urtoxazumab | humanized | diarrhoea caused by *E. coli* |

In one embodiment, the antibody is specific for an epitope associated with a non-cancer disease. In one embodiment, the disease is an autoimmune disease. In one embodiment, the disease is an allergy. In one embodiment, the disease is asthma. In one embodiment, the disease is associated with inflammation or an inflammatory response. Preferably, the disease is not an infectious disease.

Tables 4-6 depict non-limiting lists of antibodies or fusion proteins for non-oncology targets, e.g., autoimmune disease or inflammatory disease.

TABLE 4

Antibodies approved or in trials for non-oncology targets, e.g., autoimmune disease or inflammatory disease.
Antibodies

| Biologic | Type | Treatment(s) | Target(s) |
|---|---|---|---|
| abciximab | Chimeric | Cardiovascular disease | inhibition of glycoprotein IIb/IIIa |
| basiliximab | Chimeric | Transplant rejection | CD25 |
| certolizumab | Humanized | Crohn's disease; RA | TNF |
| daclizumab | Humanized | Transplant rejection | CD25 |
| eculizumab | Humanized | Paroxysmal nocturnal hemoglobinuria | C5 complement protein |
| efalizumab | Humanized | Psoriasis | CD11a |
| infliximab | Chimeric | Autoimmune disorders | TNF |
| muromonab-CD3 | Murine | Transplant rejection | T-cell CD3 receptor |
| natalizumab | Humanized | Multiple Sclerosis; Crohn's disease | α4 integrin subunit |
| omalizumab | Humanized | Asthma, eczema, allergy | IgE |
| tocilizumab/atlizumab | Humanized | Rheumatoid arthritis (RA); JIA | IL-6R |
| vedolizumab | Humanized | Crohn's disease; ulcerative colitis | α4β7 integrin |
| abrilumab | Human | inflammatory bowel disease; ulcerative colitis; Crohn's disease | α4β7 integrin |
| adalimumab | Human | RA, JIA, psoriatic arthritis, Crohn's disease, AS and plaque psoriasis | TNF |
| belimumab | Human | Systemic lupus erythematosus | BAFF |
| canakinumab | Human | Cryopyrin-associated periodic syndrome (CAPS); arthritis; gout; neonatal-onset multisystem inflammatory disease | IL-1β |
| golimumab | Human | Arthritis; Ankylosing spondylitis (AS) | TNF |
| ustekinumab | Human | Psoriatic Arthritis; Plaque Psoriasis; Crohn's disease | IL-12 and IL-23 |
| otelixizumab | chimeric/humanized | diabetes mellitus type 1 | CD3 |
| teplizumab | humanized | diabetes mellitus type 1 | CD3 |
| ocrelizumab | humanized | rheumatoid arthritis, lupus erythematosus etc. | CD20 |
| Alemtuzumab | humanized | Multiple sclerosis | CD52 |
| Mepolizumab | humanized | asthma and white blood cell diseases; Hyper-eosinophilic syndrome | IL-5 |
| Reslizumab | humanized | inflammations of the airways, skin and gastrointestinal tract; Eosinophilic oesophagitis | IL-5 |
| ranibizumab | Humanized | Macular degeneration | VEGF-A |
| Briakinumab | human | psoriasis, rheumatoid arthritis, inflammatory bowel diseases, multiple sclerosis | IL-12 and IL-23 |

TABLE 5

Fusion proteins approved or in trials for non-oncology targets, e.g., autoimmune disease or inflammatory disease
Fusion Proteins

| Biologic | Description | Treatment(s) | Target(s) |
|---|---|---|---|
| Aflibercept | VEGF receptor fragment with IgG1 Fc | Wet macular degeneration; colorectal cancer | VEGF |
| belatacept | CTLA-4 with IgG1 Fc | Organ rejection | T cell activation |
| rilonacept | IL-1R with IgG1 Fc | Cryopyrin-associated periodic syndromes; | IL-1 |
| romiplostim | Thrombopoietin-binding peptide | Thrombocytopenia | Activation of TPO |
| abatacept | Mutated CTLA-4 with IgG1 Fc | Rheumatoid arthritis | receptor CD80 and CD86 |
| alefacept | LFA-3 with IgG1 Fc | Psoriasis; transplant rejection | CD2 |
| etanercept | TNFR with IgG1 Fc | Rheumatoid arthritis; juvenile idiopathic arthritis (HA); psoriasis; ankylosing | TNF |

TABLE 5-continued

Fusion proteins approved or in trials for non-oncology targets, e.g., autoimmune disease or inflammatory disease
Fusion Proteins

| Biologic | Description | Treatment(s) | Target(s) |
|---|---|---|---|
| N/A | glucagon like peptide 1 with IgG2 | spondylitis Type I diabetes | |
| Atacicept | TACT ECD-Fc (IgG1) fusion protein, modified Fc to eliminate effector functions | Systemic lupus erythematosus; graft vs host disease | BAFF and APRIL |

TABLE 6

Other antibodies for non-oncology uses
Antibodies

| Antibody | Type | Proposed Treatment/Target |
|---|---|---|
| Alirocumab | human | hypercholesterolemia |
| Anifrolumab | human | systemic lupus erythematosus |
| Anrukinzumab | humanized | Ulcerative colitis |
| Aselizumab | humanized | severely injured patients |
| Atinumab | human | Anti-reticulon 4 |
| Atlizumab | humanized | rheumatoid arthritis |
| Atorolimumab | human | hemolytic disease of the newborn |
| Begelomab | mouse | graft versus host disease |
| Benralizumab | humanized | asthma |
| Bertilimumab | human | severe allergic disorders |
| Bimagrumab | human | myostatin inhibitor |
| Bimekizumab | humanized | arthritis |
| Blosozumab | humanized | osteoporosis |
| Bococizumab | humanized | dyslipidemia |
| Brodalumab | human | inflammatory diseases |
| Brolucizumab | humanized | psoriatic arthritis |
| Caplacizumab | humanized | thrombotic thrombocytopenic purpura, thrombosis |
| Cedelizumab | humanized | prevention of organ transplant rejections, treatment of autoimmune diseases |
| Clazakizumab | humanized | rheumatoid arthritis |
| Clenoliximab | chimeric | rheumatoid arthritis |
| Concizumab | humanized | bleeding |
| Dapirolizumab pegol | humanized | lupus |
| Dectrekumab | human | allergic rhinitis (hay fever), allergic asthma, rectal fistula in patients with Crohn's disease, oesophagitis and pulmonary fibrosis |
| Dupilumab | human | atopic diseases |
| Eldelumab | human | Crohn's disease, ulcerative colitis |
| Elsilimomab | mouse | immunosuppression |
| Enlimomab pegol | mouse | Arthritis/transplant rejection |
| Enokizumab | humanized | asthma |
| Etrolizumab | humanized | inflammatory bowel disease |
| Evinacumab | human | dyslipidemia |
| Evolocumab | human | hypercholesterolemia |
| Fanolesomab | mouse | appendicitis (diagnosis) |
| Fasinumab | human | acute sciatic pain |
| Fezakinumab | human | rheumatoid arthritis, psoriasis |
| Fletikumab | human | rheumatoid arthritis |
| Fontolizumab | humanized | Crohn's disease etc. |
| Foralumab | human | Inflammatory diseases |
| Fresolimumab | human | idiopathic pulmonary fibrosis, focal segmental glomerulosclerosis, cancer pain |
| Fulranumab | human | pain |
| Gavilimomab | mouse | graft versus host disease |
| Gevokizumab | humanized | diabetes etc. |
| Gomiliximab | chimeric | allergic asthma |
| Guselkumab | human | psoriasis |
| Idarucizumab | humanized | reversal of anticoagulant effects of dabigatran |
| Inclacumab | human | inflammation |
| Inolimomab | mouse | graft versus host disease |

TABLE 6-continued

Other antibodies for non-oncology uses
Antibodies

| Antibody | Type | Proposed Treatment/Target |
|---|---|---|
| Itolizumab | humanized | psoriasis |
| Ixekizumab | humanized | autoimmune diseases |
| Keliximab | chimeric | chronic asthma |
| Lambrolizumab | humanized | antineoplastic agent |
| Lampalizumab | humanized | Macular degeneration |
| Lebrikizumab | humanized | asthma |
| Lerdelimumab | human | reduction of scarring after glaucoma surgery |
| Ligelizumab | humanized | severe asthma and chronic spontaneous urticaria |
| Lodelcizumab | humanized | hypercholesterolemia |
| Lulizumab pegol | humanized | autoimmune diseases |
| Maslimomab | mouse | immunosuppression |
| Mavrilimumab | human | rheumatoid arthritis |
| Metelimumab | human | systemic scleroderma |
| Morolimumab | human | Anti-Rhesus factor |
| Namilumab | human | psoriasis |
| Nebacumab | human | sepsis |
| Nemolizumab | humanized | Atopic dermatitis |
| Nerelimomab | mouse | TNF inhibitor |
| Odulimomab | mouse | prevention of organ transplant rejections, immunological diseases |
| Olokizumab | humanized | Inflammatory disease |
| Opicinumab | human | multiple sclerosis |
| Orticumab | human | Inflammatory disease |
| Oxelumab | human | asthma |
| Ozanezumab | humanized | ALS and multiple sclerosis |
| Ozoralizumab | humanized | inflammation |
| Pascolizumab | humanized | asthma |
| Pateclizumab | humanized | TNF |
| Perakizumab | humanized | arthritis |
| Pexelizumab | humanized | reduction of side effects of cardiac surgery |
| Placulumab | human | Inflammatory diseases |
| Priliximab | chimeric | Crohn's disease, multiple sclerosis |
| Quilizumab | humanized | asthma |
| Ralpancizumab | humanized | dyslipidemia |
| Refanezumab | humanized | recovery of motor function after stroke |
| Rinucumab | human | neovascular age-related macular degeneration |
| Roledumab | human | anti-RhD |
| Romosozumab | humanized | osteoporosis |
| Rontalizumab | humanized | systemic lupus erythematosus |
| Rovelizumab | humanized | haemorrhagic shock etc. |
| Ruplizumab | humanized | rheumatic diseases |
| Sarilumab | human | rheumatoid arthritis, ankylosing spondylitis |
| Secukinumab | human | uveitis, rheumatoid arthritis psoriasis |
| Sifalimumab | humanized | SLE, dermatomyositis, polymyositis |
| Simtuzumab | humanized | fibrosis |
| Siplizumab | humanized | psoriasis, graft-versus-host disease (prevention) |
| Sirukumab | human | rheumatoid arthritis |
| Sonepcizumab | humanized | choroidal and retinal neovascularization |
| Sontuzumab | humanized | non-alcoholic steatohepatitis/primary sclerosing cholangitis |
| Stamulumab | human | muscular dystrophy |
| Tadocizumab | humanized | percutaneous coronary intervention |
| Talizumab | humanized | allergic reaction |
| Tanezumab | humanized | pain |
| Telimomab aritox | mouse | Immunosuppressive (linked to A chain of ricin protein) |
| Teneliximab | chimeric | Anti-CD40 |
| Tesidolumab | human | Choroiditis; Dry age-related macular degeneration; Panuveitis; Paroxysmal nocturnal haemoglobinuria; Wet age-related macular degeneration |
| TGN1412 | humanized | chronic lymphocytic leukemia, rheumatoid arthritis |
| Tildrakizumab | humanized | immunologically mediated inflammatory disorders |
| Toralizumab | humanized | rheumatoid arthritis, lupus nephritis etc. |
| Tralokinumab | human | asthma etc. |
| Tregalizumab | humanized | Anti-CD4 |
| Trevogrumab | human | muscle atrophy due to orthopedic disuse |

TABLE 6-continued

Other antibodies for non-oncology uses
Antibodies

| Antibody | Type | Proposed Treatment/Target |
| --- | --- | --- |
| | | and sarcopenia |
| Vatelizumab | humanized | Multiple sclerosis |
| Vepalimomab | mouse | inflammation |
| Visilizumab | humanized | Crohn's disease, ulcerative colitis |
| Zanolimumab | human | rheumatoid arthritis, psoriasis, T-cell lymphoma |
| Zolimomab aritox | mouse | systemic lupus erythematosus, graft-versus-host disease |

In some aspects, the nanoparticle composition further comprises a therapeutic agent. In one embodiment, the therapeutic agent is an antibiotic or antimicrobial. In one embodiment, the therapeutic agent is an anti-inflammatory agent. Such therapeutic agents are known in the art. In some aspects, the complex further comprises a sub-therapeutic amount of paclitaxel, which amount is sufficient to allow formation of the complex.

Aptamers are DNA or RNA molecules that can bind to a target molecule (e.g., a protein expressed by the cancer cell or aberrant cell). This disclosure employs aptamers that target aberrant cells, such as cancer cells or virus-infected cells. Aptamers are selected based on their relative binding affinities to the molecule of interest from a library of nucleic acids or peptides. The library can be as large as 1015 members—preferably either single strand DNA or RNA. Methodology to isolate aptamers having strong binding affinities is reported by DeGrasse, *PLoS One*, 2012, 7(3) e33410, which is incorporated herein by reference in its entirety.

Like an antibody, an aptamer can specifically bind to its target with picomolar to nanomolar affinity. Importantly, unlike antibodies, aptamers can be directly amplified by PCR. Aptamers have been widely used in many applications, including target detection, enzyme inhibition, receptor regulation, and drug delivery. Some aptamers (e.g., MACUGEN, for age-related macular degeneration) have been approved by the FDA, and several show promise towards various diseases, including cancer. See. e.g., Wu et al., Theranostics. 2015; 5(4): 322-344, which is incorporated herein by reference in its entirety.

Without being bound by theory, it is contemplated that the combination of unglycosylated or partially glycosylated (e.g., as compared to the naturally-occurring or human-derived) antibody or fusion protein may alter its binding capability to a protein core. In such cases, where the carrier-binding portion is present in a region of the antibody or fusion protein that is unglycosylated or partially glycosylated, the protein will coat or bind to the portion of an aptamer or fusion protein that interacts with the protein core (e.g., albumin), thereby reducing the immunogenicity of the binding agent while imparting increased stability and/or efficacy of the antibody, the aptamer or fusion protein in vivo.

In some embodiments, the antibody is a non-therapeutic and non-endogenous human antibody. In some embodiments, the antibody is a chimeric antibody, a non-endogenous human antibody, a humanized antibody, or non-human antibody.

In some embodiments, the chemotherapeutic drug (agent) is selected from the group consisting of abiraterone, bendamustine, bortezomib, carboplatin, cabazitaxel, cisplatin, chlorambucil, dasatinib, docetaxel, doxorubicin, epirubicin, erlotinib, etoposide, everolimus, gefitinib, idarubicin, imatinib, hydroxyurea, imatinib, lapatinib, leuprorelin, melphalan, methotrexate, mitoxantrone, nedaplatin, nilotinib, oxaliplatin, paclitaxel, pazopanib, pemetrexed, picoplatin, romidepsin, satraplatin, sorafenib, vemurafenib, sunitinib, teniposide, triplatin, vinblastine, vinorelbine, vincristine, and cyclophosphamide.

Both ABRAXANE® and albumin particles comprising other chemotherapeutic agents are disclosed by U.S. Pat. Nos. 7,758,891; 7,820,788; 7,923,536; 8,034,375; 8,138,229; 8,268,348; 8,314,156; 8,853,260; and 9,101,543, each of which is incorporated herein by reference in its entirety. In addition, carrier protein, chemotherapeutic drug, antibody conjugates, or combinations thereof are disclosed by PCT/US2015/054295 and U.S. Publication No. 2014/0178486, each of which is incorporated herein by reference in its entirety.

In some embodiments, the chemotherapeutic agent is associated with a carrier protein. In some embodiments, the complex further comprises a sub-therapeutic amount of paclitaxel.

In some embodiments, the effective amount of the chemotherapeutic drug is selected from an amount consisting of about 100 mg/m$^2$, about 105 mg/m$^2$, about 110 mg/m$^2$, about 115 mg/m$^2$, about 120 mg/m$^2$, about 125 mg/m$^2$, about 130 mg/m$^2$, about 135 mg/m$^2$, about 140 mg/m$^2$, about 145 mg/m$^2$, about 150 mg/m$^2$, about 155 mg/m$^2$, about 160 mg/m$^2$, about 165 mg/m$^2$, about 170 mg/m$^2$, about 175 mg/m$^2$, about 180 mg/m$^2$, about 185 mg/m$^2$, about 190 mg/m$^2$, about 195 mg/m$^2$, or about 200 mg/m$^2$ of the chemotherapeutic.

It is to be understood that the therapeutic agent (i.e., chemotherapeutic agent) may be located inside the nanoparticle, on the outside surface of the nanoparticle, or both. The nanoparticle may contain more than one different therapeutic agents, for example, two therapeutic agents, three therapeutic agents, four therapeutic agents, five therapeutic agents, or more. Furthermore, a nanoparticle may contain the same or different therapeutic agents inside and outside the nanoparticle.

In one aspect, the amount of chemotherapeutic agent, e.g. paclitaxel, in the nanoparticle is sufficient to allow formation of the nanoparticle. The use of sub-therapeutic amounts of paclitaxel for formation of antibody-albumin nanoparticle complexes is described, for example, in U.S. Provisional App. No. 62/384,119, which is incorporated herein by reference in its entirety.

In one embodiment, the amount of paclitaxel present in the nanoparticle composition is greater than or equal to a minimum amount capable of providing stability to the nanoparticles. In one embodiment, the amount of paclitaxel present in the nanoparticle composition is greater than or equal to a minimum amount capable of providing affinity of the at least one therapeutic agent to the protein carrier. In one embodiment, the amount of paclitaxel present in the nanoparticle composition is greater than or equal to a minimum amount capable of facilitating complex-formation of the at least one therapeutic agent and the protein carrier. In one embodiment, the weight ratio of the carrier protein and the paclitaxel of the nanoparticle composition is greater than about 9:1. In one embodiment, the weight ratio is greater than about 10:1, or 11:1, or 12:1, or 13:1, or 14:1, or 15:1, or about 16:1, or about 17:1, or about 18:1, or about 19:1, or about 20:1, or about 21:1, or about 22:1, or about 23:1, or about 24:1, or about 25:1, or about 26:1, or about 27:1, or about 28:1, or about 29:1, or about 30:1. In one embodiment, the amount of paclitaxel is equal to an minimum amount capable of providing stability to the nanoparticles. In one embodiment, the amount of paclitaxel is greater than or equal to a minimum amount capable of providing affinity of the at least one therapeutic agent to the protein carrier. In one embodiment, the amount of paclitaxel is greater than or equal to a minimum amount capable of facilitating complex-formation of the at least one therapeutic agent and the protein carrier. In any of the embodiments, the amount of paclitaxel can be less than a therapeutic amount for paclitaxel. In other words, the amount can be less than what is provided or contemplated for providing a therapeutic benefit, such as for example, a chemotherapeutic amount to effectively treat a cancer.

In one embodiment, the amount of paclitaxel present in the nanoparticle composition is less than about 5 mg/mL upon reconstitution with an aqueous solution. In one embodiment, the amount of paclitaxel present in the nanoparticle composition is less than about 4.54 mg/mL, or about 4.16 mg/mL, or about 3.57 mg/mL, or about 3.33 mg/mL, or about 3.12 mg/mL, or about 2.94 mg/mL, or about 2.78 mg/mL, or about 2.63 mg/mL, or about 2.5 mg/mL, or about 2.38 mg/mL, or about 2.27 mg/mL, or about 2.17 mg/mL, or about 2.08 mg/mL, or about 2 mg/mL, or about 1.92 mg/mL, or about 1.85 mg/mL, or about 1.78 mg/mL, or about 1.72 mg/mL, or about 1.67 mg/mL upon reconstitution with an aqueous solution.

In some embodiments any antibody, aptamer, therapeutic agent, or any combination thereof is expressly excluded.

Cancers or tumors that can be treated by the compositions and methods described herein include, but are not limited to cancers listed in the above tables and: biliary tract cancer; brain cancer, including glioblastomas and medulloblastomas; breast cancer; uterine cancer; tubal cancer; cervical cancer; choriocarcinoma; colon cancer; bladder cancer; endometrial cancer; vaginal cancer; vulvar cancer; esophageal cancer; mouth cancer; gastric cancer; kidney cancer; hematological neoplasms, including acute lymphocytic and myelogenous leukemia; multiple myeloma; AIDS associated leukemias and adult T-cell leukemia lymphoma; intraepithelial neoplasms, including Bowen's disease and Paget's disease; liver cancer (hepatocarcinoma); lung cancer; head or neck cancers or oral cancers (mouth, throat, esophageal, nasopharyngeal, jaw, tonsil, nasal, lip, salivary gland, tongue, etc.); lymphomas, including Hodgkin's disease and lymphocytic lymphomas; neuroblastomas; neuroendocrine tumors; oral cancer, including squamous cell carcinoma; adrenal cancer; anal cancer; angiosarcoma; appendix cancer; bile duct cancer; bone cancer; carcinoid tumors; soft tissue sarcoma; rhabdomyosarcoma; eye cancer; ovarian cancer, including those arising from epithelial cells, stromal cells, germ cells and mesenchymal cells, and fallopian tube cancer; gallbladder cancer; pancreas cancer; prostate cancer; rectal cancer; sarcomas, including leiomyosarcoma, rhabdomyosarcoma, liposarcoma, fibrosarcoma and osteosarcoma; skin cancer, including melanoma, Kaposi's sarcoma, basocellular cancer and squamous cell cancer; testicular cancer, including germinal tumors (seminoma, non-seminoma[teratomas, choriocarcinomas]), stromal tumors and germ cell tumors; penile cancer; hemangioendothelioma; gastrointestinal cancer; ureteral cancer; urethral cancer; spinal cancer; pituitary gland cancer; primary central nervous system (CNS) lymphoma; thyroid cancer, including thyroid adenocarcinoma and medullar carcinoma; and renal cancer including adenocarcinoma and Wilms tumor. In important embodiments, cancers or tumors include breast cancer, prostate cancer, colorectal cancer, lymphoma, multiple myeloma, and melanoma In some cases, complexes as described herein can be designed to have an average diameter that is less than 1 μm. For example, appropriate concentrations of carrier protein and antibody (or other binding agent) can be used such that complexes having an average diameter that is less than 1 μm are formed. In some cases, the complexes provided herein can have an average diameter that is between 0.1 μm and 1 μm (e.g., between 0.1 μm and 0.95 μm, between 0.1 μm and 0.9 μm, between 0.1 μm and 0.8 μm, between 0.1 μm and 0.7 μm, between 0.1 μm and 0.6 μm, between 0.1 μm and 0.5 μm, between 0.1 μm and 0.4 μm, between 0.1 μm and 0.3 μm, between 0.1 μm and 0.2 μm, between 0.2 μm and 1 μm, between 0.3 μm and 1 μm, between 0.4 μm and 1 μm, between 0.5 μm and 1 μm, between 0.2 μm and 0.6 μm, between 0.3 μm and 0.6 μm, between 0.2 μm and 0.5 μm, or between 0.3 μm and 0.5 μm). Complexes provided herein having an average diameter that is between 0.1 μm and 0.9 μm can be administered systemically (e.g., intravenously) to treat cancer or other disease located within a mammal's body.

In some cases, a complex as provided herein can have greater than 60 percent (e.g., greater than 65, 70, 75, 80, 90, 95, or 99 percent) of the complexes having a diameter that is between 0.1 μm and 0.9 μm (e.g., between 0.1 μm and 0.95 μm, between 0.1 μm and 0.9 μm, between 0.1 μm and 0.8 μm, between 0.1 μm and 0.7 μm, between 0.1 μm and 0.6 μm, between 0.1 μm and 0.5 μm, between 0.1 μm and 0.4 μm, between 0.1 μm and 0.3 μm, between 0.1 μm and 0.2 μm, between 0.2 μm and 1 μm, between 0.3 μm and 1 μm, between 0.4 μm and 1 μm, between 0.5 μm and 1 μm, between 0.2 μm and 0.6 μm, between 0.3 μm and 0.6 μm, between 0.2 μm and 0.5 μm, or between 0.3 μm and 0.5 μm). Complexes provided herein having greater than 60 percent (e.g., greater than 65, 70, 75, 80, 90, 95, or 99 percent) of the complexes with a diameter that is between 0.1 μm and 0.9 μm can be administered systemically (e.g., intravenously) to treat cancer or other disease expressing the relevant antigen located within a mammal's body.

In general, any appropriate combination of carrier protein, chemotherapy agent, and binding agent can be used as described herein. For example, an appropriate amount of carrier protein (e.g., with a chemotherapeutic drug), and an appropriate amount of binding agent can be mixed together in the same container. This mixture can be incubated at an appropriate temperature (e.g., room temperature, between 5° C. and 60° C., between 23° C. and 60° C., between 15° C. and 30° C., between 15° C. and 25° C., between 20° C. and 30° C., or between 20° C. and 25° C.) for a period of time (e.g., about 30 minutes, or between about 5 minutes and about 60 minutes, between about 5 minutes and about 45 minutes, between about 15 minutes and about 60 minutes, between about 15 minutes and about 45 minutes, between about 20 minutes and about 400 minutes, or between about 25 minutes and about 35 minutes) before being administered to a patient having a cancer.

In some cases, carrier protein nanoparticles comprising a chemotherapy agent can be contacted with a binding agent to form complexes that are stored prior to being administered to a patient. For example, a composition can be formed as described herein and stored for a period of time (e.g., days or weeks) prior to being administered to a patient.

Any appropriate method can be used to obtain complexes as described herein. Any appropriate method can be used to administer a complex as provided herein to a mammal. For example, a composition containing carrier protein/binding agent/chemotherapeutic drug complexes can be administered via injection (e.g., subcutaneous injection, intramuscular injection, intravenous injection, or intrathecal injection).

Before administering a composition containing a complex as provided herein to a mammal, the mammal can be assessed to determine whether or not the mammal has a cancer or disease expressing the relevant antigen. Any appropriate method can be used to determine whether or not a mammal has a cancer or disease expressing the relevant antigen. For example, a mammal (e.g., human) can be identified using standard diagnostic techniques. In some cases, a tissue biopsy can be collected and analyzed to determine whether or not a mammal has a cancer or disease expressing the antigen.

After identifying a mammal as having the disease or cancer, the mammal can be administered a composition containing a complex as provided herein. For example, a composition containing the complex can be administered prior to or in lieu of surgical resection of a tumor. In some cases, a composition containing a complex as provided herein can be administered following resection of a tumor.

In some cases the nanoparticle complex as described herein may be administered with an effective amount of NK or NK-92 cells. The NK or NK-92 cells may be administered to the subject concurrently with the complexes or may be administered sequentially to the subject. For example, the NK-92 cells may be administered before the complexes are administered to the subject. An effective amount of the NK or NK-92 cells can be any amount that further reduces the progression rate of a cancer or disease expressing the antigen recognized by the binding agent (e.g., antibody or aptamer), increases the progression-free survival rate, or increases the median time to progression as compared using the complexes without the NK or NK-92 cells, and preferably without producing significant toxicity to the mammal.

If a particular mammal fails to respond to a particular amount, then the amount can be increased by, for example, two fold. After receiving this higher concentration, the mammal can be monitored for both responsiveness to the treatment and toxicity symptoms, and adjustments made accordingly. The effective amount can remain constant or can be adjusted as a sliding scale or variable dose depending on the mammal's response to treatment. Various factors can influence the actual effective amount used for a particular application. For example, the frequency of administration, duration of treatment, use of multiple treatment agents, route of administration, and severity of the cancer or disease may require an increase or decrease in the actual effective amount administered.

A composition containing a complex as provided herein can be administered to a mammal in any appropriate amount, at any appropriate frequency, and for any appropriate duration effective to achieve a desired outcome (e.g., to increase progression-free survival). In some cases, a composition as provided herein can be administered to a mammal having a cancer or disease to reduce the progression rate of the cancer or disease by 5, 10, 25, 50, 75, 100, or more percent. For example, the progression rate can be reduced such that no additional cancer progression is detected.

Any appropriate method can be used to determine whether or not the progression rate of cancer is reduced. For example, the progression rate of a cancer can be assessed by imaging tissue at different time points and determining the amount of cancer cells present. The amounts of cancer cells determined within tissue at different times can be compared to determine the progression rate. After treatment as described herein, the progression rate can be determined again over another time interval. In some cases, the stage of cancer after treatment can be determined and compared to the stage before treatment to determine whether or not the progression rate was reduced.

In some cases, a composition as provided herein can be administered to a mammal having a cancer under conditions where progression-free survival is increased (e.g., by 5, 10, 25, 50, 75, 100, or more percent) as compared to the median progression-free survival of corresponding mammals having untreated cancer or the median progression-free survival of corresponding mammals having cancer treated with the carrier protein, chemotherapy agent, and the binding agent without forming complexes prior to administration. In some cases, a composition as provided herein can be administered to a mammal having a cancer to increase progression-free survival by 5, 10, 25, 50, 75, 100, or more percent as compared to the median progression-free survival of corresponding mammals having a cancer and having received the carrier protein, chemotherapy agent, carrier protein/chemotherapy agent nanoparticle (without a binding agent), or binding agent alone. Progression-free survival can be measured over any length of time (e.g., one month, two months, three months, four months, five months, six months, or longer).

In some cases, a composition containing a complex as provided herein can be administered to a mammal having a under conditions where the 8-week progression-free survival rate for a population of mammals is 65% or greater (e.g., 66%, 67%, 68%, 69%, 70%, 71%, 72%, 73%, 74%, 75%, 76%, 77%, 78%, 79%, 80% or greater) than that observed in a population of comparable mammals not receiving a composition containing complexes as provided herein. In some cases, the composition can be administered to a mammal having a cancer under conditions where the median time to progression for a population of mammals is at least 150 days (e.g., at least 155, 160, 163, 165, or 170 days).

An effective amount of a composition containing complexes as provided herein can be any amount that reduces the progression rate of a cancer or disease expressing the antigen recognized by the binding agent, increases the progression-free survival rate, or increases the median time to progression without producing significant toxicity to the mammal. If a particular mammal fails to respond to a particular amount, then the amount can be increased by, for example, two fold. After receiving this higher concentration, the mammal can be monitored for both responsiveness to the treatment and toxicity symptoms, and adjustments made accordingly. The effective amount can remain constant or can be adjusted as a sliding scale or variable dose depending on the mammal's response to treatment. Various factors can influence the actual effective amount used for a particular application. For example, the frequency of administration, duration of treatment, use of multiple treatment agents, route of administration, and severity of the cancer or disease may require an increase or decrease in the actual effective amount administered.

The frequency of administration can be any frequency that reduces the progression rate of a cancer or disease, increases the progression-free survival rate, or increases the median time to progression without producing significant toxicity to the mammal. For example, the frequency of administration can be from about once a month to about three times a month, or from about twice a month to about six times a month, or from about once every two months to about three times every two months. The frequency of administration can remain constant or can be variable during the duration of treatment. A course of treatment with a composition as provided herein can include rest periods. For example, the composition can be administered over a two week period followed by a two week rest period, and such a regimen can be repeated multiple times. As with the effective amount, various factors can influence the actual frequency of administration used for a particular application. For example, the effective amount, duration of treatment, use of multiple treatment agents, route of administration, and severity of the cancer or disease may require an increase or decrease in administration frequency.

An effective duration for administering a composition provided herein can be any duration that reduces the progression rate of a cancer or disease, increases the progression-free survival rate, or increases the median time to progression without producing significant toxicity to the mammal. Thus, the effective duration can vary from several days to several weeks, months, or years. In general, the effective duration for the treatment of a cancer or disease can range in duration from several weeks to several months. In some cases, an effective duration can be for as long as an individual mammal is alive. Multiple factors can influence the actual effective duration used for a particular treatment. For example, an effective duration can vary with the frequency of administration, effective amount, use of multiple treatment agents, route of administration, and severity of the cancer or disease.

A composition containing carrier protein/chemotherapy agent/binding agent complexes as provided herein can be in any appropriate form. For example, a composition provided herein can be in the form of a solution or powder with or without a diluent to make an injectable suspension. A composition also can contain additional ingredients including, without limitation, pharmaceutically acceptable vehicles. A pharmaceutically acceptable vehicle can be, for example, saline, water, lactic acid, mannitol, or combinations thereof.

After administering a composition provided herein to a mammal, the mammal can be monitored to determine whether or not the cancer or disease was treated. For example, a mammal can be assessed after treatment to determine whether or not the progression rate of the cancer or disease was reduced (e.g., stopped). As described herein, any method can be used to assess progression and survival rates.

OTHER EMBODIMENTS

It is to be understood that while the invention has been described in conjunction with the detailed description thereof, the foregoing description is intended to illustrate and not limit the scope of the invention. Other aspects, advantages, and modifications are within the scope of the following claims.

EXAMPLES

One skilled in the art would understand that descriptions of making and using the particles described herein is for the sole purpose of illustration, and that the present disclosure is not limited by this illustration.

Example 1. Albumin Nanoparticles Comprising Rituximab (AR160)

The particles are synthesized by adding between about 5 mg and about 20 mg of rituximab (or non-specific IgG) to 20 mg of ABRAXANE. Saline is then added to a final volume of 2 ml for a final concentration of 10 mg/ml ABRAXANE, and the mixture is allowed to incubate at room temperature for 30 minutes to allow particle formation. Particles average about 160 nm and are termed "AR160" nanoparticles.

Optionally, the composition is divided into aliquots and frozen at −80° C. Once frozen the aliquots are optionally lyophilized overnight with the Virtis 3L benchtop lyophilizer (SP Scientific, Warmister, Pa.) with the refrigeration on. A lyophilized preparation is generated.

The dried aliquots are stored at room temperature. These samples are reconstituted in saline at room temperature for 30 minutes, followed by centrifugation for 7 minutes at 2000×g. The resulting sample is then resuspended in the appropriate buffer, as needed.

Example 2. Evaluation of Tumor Uptake of AR160

Mice were injected via subcutaneous injection with lymphoma cells and tumors allowed to form. Mice received intravenous (IV) injection of equal amounts of alexaflor 750-labeled ABRAXANE (ABX), ABRAXANE coated with non-specific antibodies (AB IgG), or AR160.

Twenty-four hours after IV injection, tumor accumulation of the respective treatments was determined based on a fluorescence threshold. Background was determined based on a region of the mouse without a tumor. FIG. 1 is a graphical representation of background and tumor fluorescence. Table 8 indicates the numerical values for each, including tumor-associated fluorescence (average radiant efficiency from the tumor minus background). Addition of rituximab to the ABRAXANE nanoparticle (AR160) results in a nearly 100% increase in tumor uptake of ABRAXANE.

TABLE 8

Average Radiant Efficiency and Adjusted Tumor-Associated Fluorescence

|  | Background | Tumor | Tumor-associated Fluorescence |
| --- | --- | --- | --- |
| ABX | 1.541 | 2.09 | 0.549 |
| AB IgG | 1.4005 | 1.99 | 0.5895 |
| AR160 | 1.545 | 2.637 | 1.092 |

What is claimed is:

1. A method for providing an acceptable therapeutic index of a chemotherapeutic drug targeting cancer cells, which method comprises:
   a) combining a therapeutically effective amount of said drug with a biocompatible protein carrier, wherein the drug has an unacceptable therapeutic index when administered alone;
   b) forming a complex with said carrier and an effective amount of an anti-CD20 antibody which has specificity to a CD20 antigen on said cancer cells, wherein said anti-CD20 antibodies populate the surface of said complex and retain binding specificity; and
   c) administering said complex to a patient, wherein said administration enhances delivery of said drug to said cells and reduces one or more side effects of said drug, thereby increasing the therapeutic index of said drug to provide an acceptable therapeutic index.

2. The method of claim 1, wherein the protein carrier is selected from the group consisting of albumin, gelatin, elastin, gliadin, legumin, zein, soy protein, milk protein, and whey protein.

3. The method of claim 2, wherein the protein carrier is albumin.

4. The method of claim 3, wherein the complex further comprises an effective amount of paclitaxel to form said complex.

5. The method of claim 4, wherein the amount of paclitaxel is between 0.1 mg/m$^2$ and 50 mg/m$^2$.

6. A method for providing an acceptable therapeutic index of a chemotherapeutic drug targeting tumor cells, which method comprises:
   a) combining a therapeutically effective amount of said drug with an albumin carrier, wherein the drug has an unacceptable therapeutic index when administered alone;
   b) forming a complex with said carrier and an effective amount of an anti-CD20 antibody which has specificity to a CD20 antigen on said tumor cells, wherein said anti-CD20 antibodies populate the surface of said complex and retain binding specificity; and
   c) administering said complex to a patient wherein said administration enhances delivery of said drug to said tumor cells and reduces one or more side effects of said drug, thereby increasing the therapeutic index of said drug.

7. The method of claim 6, wherein the complex further comprises an effective amount of paclitaxel to form said complex.

8. The method of claim 7, wherein the amount of paclitaxel is between 0.1 mg/m$^2$ and 50 mg/m$^2$.

9. The method of claim 1, wherein said complex is less than 1 micron in diameter.

10. The method of claim 1, wherein drug-related toxicity is reduced.

11. A method for providing an acceptable therapeutic index of a chemotherapeutic drug targeting aberrant mammalian cells, which method comprises:
   a) combining a therapeutically effective amount of said drug with a biocompatible protein carrier, wherein the drug has an unacceptable therapeutic index when administered alone;
   b) forming a complex with said carrier and an effective amount of anti-CD20 antibody having specificity to said aberrant cells, wherein said anti-CD20 antibody populates the surface of said complex and retains specificity and further wherein said anti-CD20 antibody has a protein carrier-binding portion; and
   c) administering said complex to a patient, wherein said administration enhances delivery of said drug to said cells and reduces one or more side effects of said drug, thereby increasing the therapeutic index of said drug.

12. The method of claim 11, wherein the aberrant mammalian cells are selected from the group consisting of cancer cells, autoimmune disease-related cells, inflammatory disease-related cells, virus-infected cells, and bacteria-infected cells.

13. The method of claim 11, wherein the protein carrier is selected from the group consisting of albumin, gelatin, elastin, gliadin, legumin, zein, soy protein, milk protein, and whey protein.

14. The method of claim 12, wherein the protein carrier is albumin.

15. The method of claim 13, wherein the complex further comprises an effective amount of paclitaxel to form said complex.

16. The method of claim 14, wherein the amount of paclitaxel is between 0.1 mg/m$^2$ and 50 mg/m$^2$.

* * * * *